(12) United States Patent
Hollinshead et al.

(10) Patent No.: US 6,395,735 B2
(45) Date of Patent: May 28, 2002

(54) PHARMACEUTICAL COMPOUNDS

(75) Inventors: Sean Patrick Hollinshead, Durham; Philip Floyd Hughes, Chapel Hill; Jose Serafin Mendoza; Joseph Wendell Wilson, both of Durham, all of NC (US); Bret Eugene Huff, Mooresville, IN (US); Charles Howard Mitch, Columbus, IN (US); Michael Alexander Staszak; John Stanley Ward, both of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/740,380

(22) Filed: Dec. 19, 2000

Related U.S. Application Data

(62) Division of application No. 09/116,408, filed on Jul. 16, 1998, now abandoned.
(60) Provisional application No. 60/053,404, filed on Jul. 22, 1997.

(51) Int. Cl.[7] .................... A61K 31/155; C07C 257/12; C07C 257/14
(52) U.S. Cl. .................... 514/237.8; 514/331; 514/428; 514/637; 544/159; 544/165; 546/234; 548/569; 564/245
(58) Field of Search .......................... 564/245; 544/165, 544/159; 546/234; 548/569; 514/237.8, 331, 428, 637

(56) References Cited

U.S. PATENT DOCUMENTS

| | | | |
|---|---|---|---|
| 3,539,631 A | 11/1970 | Pallos et al. | 564/428 |
| 4,775,695 A | 10/1988 | Crage, Jr. et al. | 514/637 |
| 5,712,171 A | 1/1998 | Zambias et al. | 436/518 |
| 5,736,412 A | 4/1998 | Zambias et al. | 436/518 |
| 6,211,364 B1 | 4/2001 | Huff et al. | 544/106 |

FOREIGN PATENT DOCUMENTS

| | | |
|---|---|---|
| JP | 61-60610 | 3/1986 |
| WO | WO 95/18617 | 1/1994 |
| WO | WO/97/25983 | 7/1997 |
| WO | WO/99/04778 | 2/1999 |

OTHER PUBLICATIONS

Oshiro et al.; *J. Med. Chem.*; 1991, vol. 34, pp. 2004–2013; Novel Cerebroprotective Agents with Central Nervous System Stimulating Activity. 1. Synthesis and Pharmacology of 1–Amino–7–hydroxyindan Derivatives.

*Primary Examiner*—Richard L. Raymond
(74) *Attorney, Agent, or Firm*—David M. Stemerick; Daniel Collins

(57) ABSTRACT

The present invention provides novel indane-like compounds which can be useful for treating psychosis and other conditions associated with the modulation of a muscarinic receptor. The invention provides formulations and methods for using the novel compounds.

11 Claims, No Drawings

PHARMACEUTICAL COMPOUNDS

This application is a divisional of U.S. Ser. No. 09/116,408, filed Jul. 16, 1998, now abandoned, which claims the benefit of U.S. Provisional Application No. 60/053,404, filed Jul. 22, 1997.

FIELD OF THE INVENTION

The present invention relates to novel indane-like compounds and to formulations containing such indane-like compounds as an active ingredient for pharmaceutical or veterinary use.

BACKGROUND OF THE INVENTION

Currently there are many drugs available for the treatment of disorders of the central nervous system. Amongst these drugs is a category known as antipsychotics for treating serious mental conditions such as psychosis, including but not limited to schizophrenia and schizophreniform illnesses. The skilled artisan will recognize that these psychotic conditions are characterized by hallucinations, delusions, or grossly disorganized behavior which indicate that the patient suffers from gross impairment in reality testing. Drugs having said antipsychotic activity can be useful for treating a variety of important psychotic disorders. The drugs commercially available for such conditions are often associated with undesirable side effects. There is a need for additional therapeutic choices to control or eliminate the symptoms in the safest and most effective way.

Furthermore, patients often do not respond or only partially respond to present drug treatment. and estimates of such partial- or non-responders has varied between 40% and 80% of those treated.

Ever since antipsychotics were introduced it has been observed that patients are liable to suffer from drug-induced extrapyramidal symptoms which include and tardive dystonia. The Simpson Angus Scale, Barnes Akathisia Rating Scale and Abnormal Involuntary Movement Scale (AIMS) are well known scales for assessing extrapyramidal symptoms. The great majority of drugs available for treatment of schizophrenia are prone to produce these extrapyramidal side effects when used at dosages that yield a beneficial effect on the symptoms of the disease. The severity of adverse events and/or lack of efficacy in a considerable number of patients frequently results in poor compliance or termination of treatment.

Many of the drugs are associated with a sedative effect and may also have an undesirable influence on the affective symptoms of the disease, causing depression. In some instances long term use of the drug leads to irreversible conditions, such as the tardive dyskinesia and tardive dystonia referred to supra.

A widely-used antipsychotic, haloperidol, is one such drug, which has been reported as causing a high incidence of extrapyramidal symptoms and may also cause tardive dyskinesia. More recently, clozapine, one of a large group of heterocyclic antipsychotics, has been introduced with the claim that it is free from extrapyramidal effects. However, the compound was found to cause agranulocytosis in some patients, a condition resulting in a lowered white blood cell count which can be life-threatening, and it may now only be employed under very strict medical observation and supervision.

The cholinergic deficits observed in Alzheimer's disease have given rise to the cholingeric hypothesis of dementia and spawned many efforts to develop therapies based on enhancement of central cholinergic transmission. The greatest efforts have focused on the use of acetylcholinesterase inhibitors and directly acting cholinomimetic drugs, but the results of clinical trials have been generally disappointing, potentially because the side effects seen with these agents prevent therapeutic doses from being employed. These intolerable side effects might be avoided by developing drugs that are functionally selective for muscarinic receptor subtypes.

Four pharmacologically distinct muscarinic receptor subtypes have been identified and designated $M_1$–$M_4$. Five genetically distinct human muscarinic receptors designated $m_1$–$m_5$ have been cloned and characterized. The relationship between the two classifications are: $M_1=m_1$, $M_2=m_2$, $M_3=m_3$, and $M_4=m_4$. These muscarinic receptor subtypes are differentially located in the brain with high levels of the $m_1$–$m_3$ receptors being located in the cortex and hippocampus, areas of the brain normally associated with cognition and learning.

Therefore, new compounds having antipsychotic activity as well as compounds which are agonists for the muscarinic receptors are highly desired.

SUMMARY OF THE INVENTION

The present invention provides a compound of the Formula I:

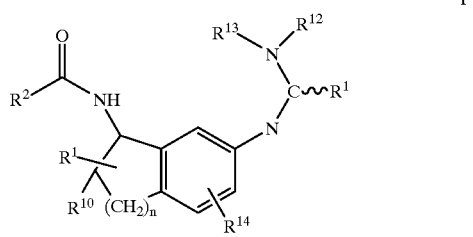

$R^1$ is selected from the group consisting of hydrogen, —$OR^4$, —$SR^5$, $C_1$–$C_3$ alkyl, $C_2$–$C_3$ alkenyl, halo, —CN, $S(O)_{m2}$, —$COR^{4b'}$, and —OC(O)—$R^{15}$;

m2 is from 0 to 2;

$R^2$ is selected from the group consisting of $C_1$–$C_{10}$ alkyl, substituted $C_1$–$C_{10}$ alkyl, $C_2$–$C_{10}$ alkenyl, substituted $C_2$–$C_{10}$ alkenyl, $C_3$–$C_8$ cycloalkyl, substituted $C_3$–$C_8$ cycloalkyl, aryl, substituted aryl, heteroaryl, substituted heteroaryl, heterocyclic, and substituted heterocyclic;

$R^4$ is hydrogen, $C_1$–$C_3$ alkyl;

$R^5$ is hydrogen, $C_1$–$C_3$ alkyl;

$R^{10}$ is selected from the group consisting of hydrogen, carbonyl, halo, and $C_1$–$C_3$ alkyl;

$R^{11}$ is selected from the group consisting of hydrogen and $C_1$–$C_3$ alkyl;

$R^{12}$ is independently selected from the group consisting of hydrogen, $C_1$–$C_{10}$ alkyl, and aryl;

$R^{13}$ is independently selected from the group consisting of hydrogen, $C_1$–$C_{10}$ alkyl, and aryl; or $R^{12}$ and $R^{13}$ together with the nitrogen to which they are attached form a group of the formula II:

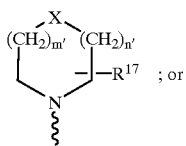

II' wherein the II' group is a group of Formula II which is unsaturated; or $R^{11}$ and $R^{12}$ together with the nitrogen and carbon to which they are bound can join to form a three to six membered ring;

$R^{14}$ is selected from the group consisting of H, halo, $C_1$–$C_3$ alkyl, $S(O)_{m3}$ and —$OR^{16}$;

$R^{15}$ is $C_1$–$C_3$ alkyl or aryl;

$R^{16}$ is $C_1$–$C_3$ alkyl;

$R^{17}$ is independently selected from the group consisting of hydrogen, —$OR^{4'}$, —$SR^{5'}$, $C_1$–$C_3$ alkyl, $C_2$–$C_3$ alkenyl, halo, —CN, $S(O)_{m2'}$, —$COR^{4b}$, and —OC(O)—$R^{15'}$;

$R^{4b}$ and $R^{4b'}$ are each independently selected from hydrogen and $C_1$–$C_3$ alkyl;

$R^{15'}$ is $C_1$–$C_3$ alkyl or aryl;

m2' is 0 to 2;

$R^{4'}$ is hydrogen, $C_1$–$C_3$ alkyl;

$R^{5'}$ is hydrogen, $C_1$–$C_3$ alkyl;

m2 is 0 to 2;

X is selected from the group consisting of $CH_2$, O, S, NH, carbonyl, and a bond;

n' is 0 to 2;

m' is 0 to 2;

m3 is 0 to 2;

n is 0 to 3; or a pharmaceutically acceptable salt or solvate thereof.

Further, the invention provides a method for treating psychosis comprising administering a compound of Formula I to a mammal in need of such treatment.

Additionally, the present invention provides a method for interacting with a muscarinic receptor comprising administering a compound of Formula I. Finally, the invention provides a formulation containing a compound of Formula I as an active ingredient.

Further this invention provides compounds of the Formula III

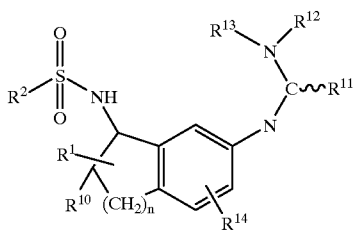

$R^1$ is selected from the group consisting of hydrogen, —$OR^4$, —$SR^5$, $C_1$–$C_3$ alkyl, $C_2$–$C_3$ alkenyl, halo, —CN, $S(O)_{m2}$, —$COR^{4b'}$, and —OC(O)—$R^{15}$;

m2 is from 0 to 2;

$R^2$ is selected from the group consisting of $C_1$–$C_{10}$ alkyl, substituted $C_1$–$C_{10}$ alkyl, $C_2$–$C_{10}$ alkenyl, substituted $C_2$–$C_{10}$ alkenyl, $C_3$–$C_8$ cycloalkyl, substituted $C_3$–$C_8$ cycloalkyl, aryl, substituted aryl, heteroaryl, substituted heteroaryl, heterocyclic, and substituted heterocyclic;

$R^4$ is hydrogen, $C_1$–$C_3$ alkyl;

$R^5$ is hydrogen, $C_1$–$C_3$ alkyl;

$R^{10}$ is selected from the group consisting of hydrogen, carbonyl, halo, and $C_1$–$C_3$ alkyl;

$R^{11}$ is selected from the group consisting of hydrogen and $C_1$–$C_3$ alkyl;

$R^{12}$ is independently selected from the group consisting of hydrogen, $C_1$–$C_{10}$ alkyl, and aryl;

$R^{13}$ is independently selected from the group consisting of hydrogen, $C_1$–$C_{10}$ alkyl, and aryl; or $R^{12}$ and $R^{13}$ together with the nitrogen to which they are attached form a group of the formula II:

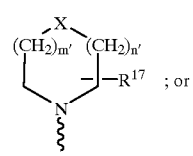

II' wherein the II' group is a group of Formula II which is unsaturated; or $R^{11}$ and $R^{12}$ together with the nitrogen and carbon to which they are bound can join to form a three to six membered ring;

$R^{14}$ is selected from the group consisting of H, halo, $C_1$–$C_3$ alkyl, $S(O)_{m3}$ and —$OR^{16}$;

$R^{15}$ is $C_1$–$C_3$ alkyl or aryl;

$R^{16}$ is $C_1$–$C_3$ alkyl;

$R^{17}$ is independently selected from the group consisting of hydrogen, —$OR^{4'}$, —$SR^{5'}$, $C_1$–$C_3$ alkyl, $C_2$–$C_3$ alkenyl, halo, —CN, $S(O)_{m2'}$, —$COR^{4b}$, and —OC(O)—$R^{15'}$;

$R^{4b}$ and $R^{4b'}$ are each independently selected from hydrogen and $C_1$–$C_3$ alkyl;

$R^{15'}$ is $C_1$–$C_3$ alkyl or aryl;

m2' is 0 to 2;

$R^{4'}$ is hydrogen, $C_1$–$C_3$ alkyl;

$R^{5'}$ is hydrogen, $C_1$–$C_3$ alkyl;

m2 is 0 to 2;

X is selected from the group consisting of $CH_2$, O, S, NH, carbonyl, and a bond;

n' is 0 to 2;

m' is 0 to 2;

m3 is 0 to 2;

n is 0 to 3; or a pharmaceutically acceptable salt or solvate thereof.

Additionally, this invention provides a formulation comprising a compound of Formula III and one or more pharmaceutically acceptable excipients or carriers therefor.

Also included is a method for treating a condition associated with the modulation of a muscarinic receptor comprising administering an effective amount of a compound of Formula III to a mammal in need of such treatment.

Additionally, provided is a compound of Formula IV

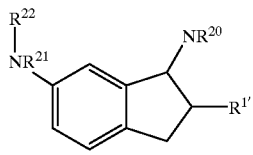

IV $R^{21}$ and $R^{22}$ are selected from H and O;

$R^{20}$ is selected from amine protecting groups;

$R^{1'}$ is selected from the group consisting of —$OR^4$, —$SR^5$, $C_1$–$C_3$ alkyl, $C_2$–$C_3$ alkenyl, halo, —CN, $S(O)_{m2}$, —$COR_{4b'}$, and —OC(O)—$R^{15}$;

m2 is 0 to 2;

$R^4$ and $R^{4b'}$ are each independently selected from hydrogen and $C_1$—$C_3$ alkyl;

$R^5$ is selected from hydrogen and $C_1$–$C_3$ alkyl;

$R^{15}$ is $C_1$–$C_3$ alkyl or aryl;

or a pharmaceutically acceptable salt or solvate thereof.

Further provided is a compound of the Formula V

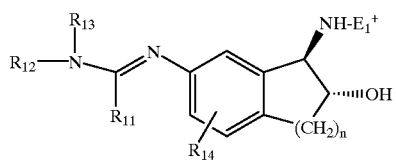

V $E_1^+$ is selected from the group consisting of $C_1$–$C_{10}$ alkyl, substituted $C_1$–$C_{10}$ alkyl, $C_2$–$C_{10}$ allkenyl, substituted $C_2$–$C_{10}$ alkenyl, $C_3$–$C_8$ cycloalkyl, substituted $C_3$–$C_8$ cycloalkyl, aryl, substituted aryl, heteroaryl, substituted heteroaryl, heterocyclic, substituted heterocyclic, and aryl electrophile;

R groups are as defined above;

or a pharmaceutically acceptable salt or solvate thereof.

Further, the invention provides a method for treating psychosis comprising administering a compound of Formula V to a mammal in need of such treatment.

Additionally, the present invention provides a method for interacting with a muscarinic receptor comprising administering a compound of Formula V.

Finally, the invention provides a formulation containing a compound of Formula V as an active ingredient.

DETAILED DESCRIPTION OF THE INVENTION

The term "treating" as used herein includes prophylaxis of the named physical and/or mental condition or amelioration or elimination of the developed physical and/or mental condition once it has been established.

The substituent of Formula II can be from a 3- member to 8 member ring. The substituent of Formula II' is unsaturated. Formula II' is optionally aromatic, but is in no way required to be aromatic. It may be preferred that Formula II' contains from one to two double bonds.

The term "interacting with a muscarinic receptor" refers to a compound acting as a muscarinic receptor agonist, antagonist, or partial agonist. Most preferably, the compounds of this invention will act as an agonist of a muscarinic receptor. It is especially preferred that a compound of this invention will selectively interact with a muscarinic receptor subtype, preferably a m1 or m4 muscarinic receptor subtype. Further it is particularly preferred that a compound of this invention will act as a selective muscarinic receptor agonist, preferably a selective m1 or m4 muscarinic receptor agonist.

The terms "$C_1$–$C_m$ alkyl" wherein m=2–10, as used herein, represent a branched or linear alkyl group having from one to the specified number of carbon atoms. For example, typical $C_1$–$C_6$ alkyl groups include methyl, ethyl, n-propyl, iso-propyl, butyl, iso-butyl, sec-butyl, tert-butyl, pentyl, hexyl and the like. The term "substituted $C_1$–$C_m$ alkyl" refers to an alkyl group which is substituted with from one to five selected from the group consisting of $C_2$–$C_6$ alkenyl, halo, —$CF_3$, —$OR^{4a}$, —$SR^{5a}$, —$CO_2R^{6a}$, halo, $C_3$–$C_8$ cycloalkyl, substituted $C_4$–$C_8$ cycloalkyl, and —CN; wherein 4a, 5a, and 6a are each independently selected from the group consisting of hydrogen, $C_1$–$C_3$ alkyl, aryl and substituted aryl. The term "carbonyl" has the meaning commonly attributed to the term by the skilled artisan. For example, =O.

The terms "$C_2$–$C_n$ alkenyl" wherein n=3–10, as used herein, represents an olefinically unsaturated branched or linear group having from 2 to 10 carbon atoms and at least one double bond. The groups can be branched or straight chain. Examples of such groups include 1-propenyl, 2-propenyl (—$CH_2$—CH=$CH_2$), 1-butenyl (—CH=CHCH$_2$CH$_3$), 1,3-butadienyl (—CH=CHCH=CH$_2$), hexenyl, pentenyl, and the like.

The terms "halide", "halogen", and "halo" include fluorine, chlorine, bromine, and iodine. The preferred halogen is chlorine.

The term "$C_3$–$C_n$ cycloalkyl" wherein n=4–8, represents cyclopropyl, cyclobutyl, cyclopentyl, cyclohexyl, cycloheptyl, cyclooctyl, and the like. The term "hererocyclic" refers to a heterocyclic ring having from four to eight members and from one to three non-carbon atoms selected from the group consisting of N, O, and S; or a combination thereof, and which heteroaryl group is optionally fused with a phenyl group.

The term "substituted heterocyclic" refers to a heterocyclic group which may be substituted with from one to three substituents selected from the group consisting of halogen (s), —$CF_3$, $NO_2$, —CN, $C_{1-15}$-alkyl, $C_{2-5}$-alkenyl, $C_{2-5}$-alkynyl, —$COR^{6a}$, —$OR^{4a}$, —$SR^{5a}$, $C_3$–$C_8$ cycloalkyl, $C_5$–$C_8$ cycloalkenyl, substituted $C_3$–$C_8$ cycloalkyl, substituted $C_5$–$C_8$ cycloalkenyl, and aryl; wherein 4a, 5a, and 6a are each independently selected from hydrogen, —$CF_3$, $C_1$–$C_3$ alkyl, aryl, and —$C_1$–$C_3$ alkyl-aryl.

As used herein the term "amine protecting group" refers to protecting groups such as those discussed in Theodora W. Greene, Protective Groups in Organic Synthesis, (Wiley, 1981) pp. 218–287. Especially preferred amine protecting groups are carbamates. One particularly preferred amine protecting group is BOC. The term "substituted($C_5$–$C_n$) cycloalkyl" refers to a cycloalkyl group as described supra wherein the cycloalkyl group may be substituted with from one to four substituents independently selected from the group consisting of hydrogen, $C_1$–$C_6$ alkyl, $C_3$–$C_8$ cycloalkyl, $NO_2$, halo, halo($C_1$–$C_6$)alkyl, halo($C_2$–$C_6$) alkenyl, $C_2$–$C_6$ alkenyl, $C_3$–$C_8$ cycloalkyl-($C_1$–$C_3$)alkyl, $C_5$–$C_8$ cycloalkenyl, $C_5$–$C_8$ cycloalkenyl-($C_1$–$C_3$)alkyl, $COR_{5a}$, $C_1$–$C_{10}$ alkanoyl, $C_7$–$C_{16}$ arylalkyl, $CO_2R_{5a}$, ($C_1$–$C_6$ alkyl)$_m$amino, —$SR_{5a}$, and $OR_{5a}$; wherein 5a is selected from hydrogen and $C_1$–$C_3$ alkyl; m is from one to two.

The term "$C_3$–$C_8$ cycloalkyl-($C_1$–$C_3$)alkyl" represents a linear alkyl group substituted at a terminal carbon with a $C_3$–$C_8$ cycloalkyl group. Typical cycloalkylalkyl groups include cyclohexylethyl, cyclohexylmethyl, 3-cyclopentylpropyl, and the like.

The term "$C_5$–$C_8$ cycloalkenyl" represents an olefinically unsaturated ring having five to eight carbon atoms, eg., cyclohexadienyl, cyclohexenyl, cyclopentenyl, cycloheptenyl, cyclooctenyl, cyclohexadienyl, cycloheptadienyl, cyclooctatrienyl and the like. The cycloalkenyl group may be substituted with from one to four substituents selected from the group consisting of hydrogen, $C_1$–$C_6$ alkyl, $NO_2$, halo, halo($C_1$–$C_6$)alkyl, halo($C_2$–$C_6$) alkenyl, $C_2$–$C_6$ alkenyl, ($C_1$–$C_6$ alkyl)$_m$amino, $COR_5$, $C_1$–$C_{10}$ alkanoyl, $OR_5$, $CO_2R_5$, —$SR_5$, and $C_7$–$C_{16}$ arylalkyl.

The term "$C_5$–$C_8$ cycloalkenyl-($C_1$–$C_3$)alkyl" represents a linear $C_1$–$C_3$ alkyl group substituted at a terminal carbon with a $C_5$–$C_8$ alkenyl group. As used herein the term "carboxy" refers to a substituent having the common meaning understood by the skilled artisan, wherein the point of attachment may be through the carbon or oxygen atom of the group.

As used herein the term "aryl" means an organic radical derived from an aromatic hydrocarbon by the removal of one atom. For example, the term includes, but is in no way limited to biphenyl, phenyl or naphthyl. The term "aryl" refers to hydrocarbon aryl groups. Most preferably, aryl refers to $C_6$–$C_{10}$ aryl, wherein the aryl ring system, including any alkyl substitutions, comprises from 6 to 10 carbon atoms; e.g., phenyl, 3,3-dimethylphenyl, naphthyl, and the like. The aryl radical may be substituted by one or two $C_1$–$C_6$ straight or branched alkyl. The aryl group may be fused with a heteroaryl or heterocyclic.

"Substituted aryl" refers to an aryl group which may be substituted with from one to three substituents selected from the group consisting of halogen(s), —$CF_3$, $NO_2$, —CN, $C_{1-15}$-alkyl, $C_{2-5}$-alkenyl, $C_{2-5}$-alkynyl, —$COR^{6a}$, —$OR^{4a}$, —$SR^{5a}$, $C_3$–$C_8$ cycloalkyl, $C_5$–$C_8$ cycloalkenyl, substituted $C_3$–$C_8$ cycloalkyl, substituted $C_5$–$C_8$ cycloalkenyl, and aryl; wherein 4a, 5a, and 6a are each independently selected from hydrogen, —$CF_3$, $C_1$–$C_3$ alkyl, aryl, and —$C_1$–$C_3$ alkylaryl. The substituents may be located at any available position on the ring, provided that there is not more than one substituent selected from the group consisting of aryl, $C_3$–$C_8$ cycloalkyl, substituted $C_3$–$C_8$ cycloalkyl, $C_5$–$C_8$ cycloalkenyl, and substituted $C_5$–$C_8$ cycloalkenyl.

As used herein, the phrase "heteroaryl" means an aryl group containing from one to three N, O or S atom(s) or a combination thereof, and which heteroaryl group is optionally fused with a phenyl group. The phrase "heteroaryl" includes, but is not limited to, 5-membered heteroaryls having one hetero atom (e.g. thiophenes, pyrroles, furans); 5-membered hetaryls having two heteroatoms in 1,2 or 1,3 positions (e.g. oxazoles, pyrazoles, imidazoles, thiazoles, purines); 5-membered heteroaryls having three heteroatoms (e.g. triazoles, thiadiazoles); 5-membered heteroaryls having 3-heteroatoms; 6-membered heteroaryls with one heteroatom (e.g. pyridine, quinoline, isoquinoline, phenanthrine, 5,6-cycloheptenopyridine); 6-membered heteraryls with two heteroatoms (e.g. pyridazines, cinnolines, phthalazines, pyrazines, pyrimidines, quinazolines); 6-membered heteroaryls with three heteroatoms (e.g. 1,3,5-triazine); and 6-member heteroaryls with four heteroatoms. Particularly preferred are benzothiophenes, pyridines, and furans. Most preferredly, the heteroaryl group is a four to eight membered ring.

The term "substituted heteroaryl" refers to a heteroaryl group which is substituted at carbon or nitrogen atom(s) with $C_{1-6}$-alkyl, —$CF_3$, phenyl, benzyl, substituted aryl or thienyl, or a carbon atom in the heteroaryl group together with an oxygen atom form a carbonyl group. Such substituted heteroaryl may optionally be fused with a phenyl group.

The term "$C_7$–$C_{16}$ arylalkyl" represents an aryl-($C_1$–$C_{10}$) alkyl substituent wherein the alkyl group is linear, such as but not limited to, benzyl, phenethyl, 3-phenylpropyl, or phenyl-t-butyl; or branched. The aryl alkyl moiety is attached to the parent nucleusvia the alkyl group.

The term "organic solvent" includes solvents containing carbon, such as halogenated hydrocarbons, ether, toluene, xylene, benzene, and tetrahydrofuran. The term "agitate" includes such techniques as stirring, centrifugation, mixing, and other similar methods.

The term "ligand" refers to compounds that are bound by the designated receptor. Compounds useful as ligands may be used to occupy the stated receptor site or may act as a selective agonist at the stated receptor site.

The abbreviations used herein have their accepted meaning, unless stated otherwise. Such accepted meaning shall be the meaning attributed to such term by the skilled artisan or the American Chemical Society.

The terms "MeO" and "EtO" refer to methoxy and ethoxy substituents which are bound to the parent molecule through the oxygen.

A method for generating the indane scaffold used in this invention for compound forming purposes comprises the following sequential steps:

1. Nitration of indanone starting yields nitroindanone which is then separated from minor component byproducts.
2. The product of step 1 is reduced to give the corresponding alcohol.
3. The product of step 2 is then subjected to an acid catalyzed dehydration to give the corresponding indene.
4. The double bond of the product of step 3 is oxidized to give the epoxide.
5. The product epoxide 4 is then reacted with ammonium hydroxide to give the amino alcohol.
6. The amino alcohol of step 5 is protected with a conventional protecting group.

The preceding method of indane scaffold preparation is further illustrated by the following reaction scheme:

INDAN SCAFFOLD FORMATION

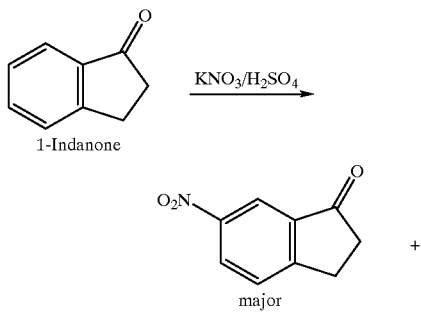

-continued

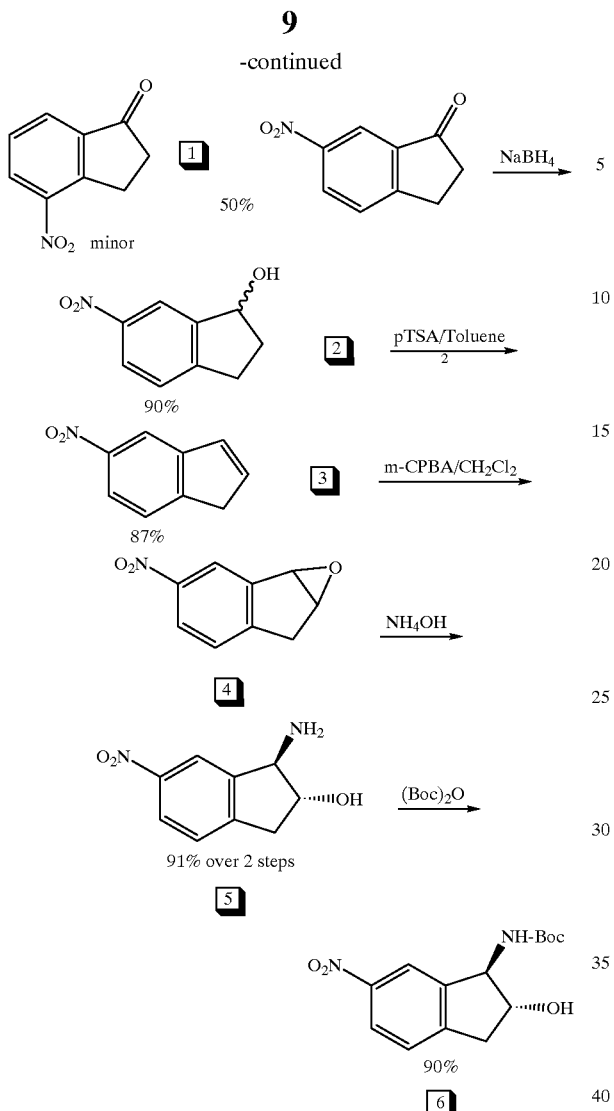

The formation of indane compounds in these libraries is accomplished using polymer bound reaction schemes generally described as follows:

A) A polymer bearing a carboxylic acid functionality is coupled with the protected indane of the following formula:

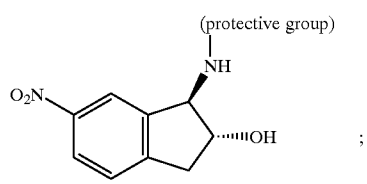

B) The reactants of step (A) are coupled;
C) The product of step (B) is deprotected resulting in an amine functional indane bound to a resin support;
D) The product of step Ⓒ is acylated to attach a first diverse group, $E_1^+$;
E) The product of step (D) is reduced to give the corresponding aniline;
F) The product of step (E) is again acylated to attach a second diverse group, $E_2^+$;

G) Cleavage with a base of the product of step (E) from the polymer results in the formation of the product characterized by the formula:

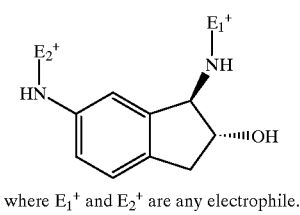

where $E_1^+$ and $E_2^+$ are any electrophile.

INDANE LIBRARY AND COMPOUND FORMING PROCESS DESCRIPTION

The process steps, more fully described below in the Preparation Section, are illustrated by the following reaction Scheme IA:

Scheme IA
SOLID PHASE INDAN CHEMISTRY

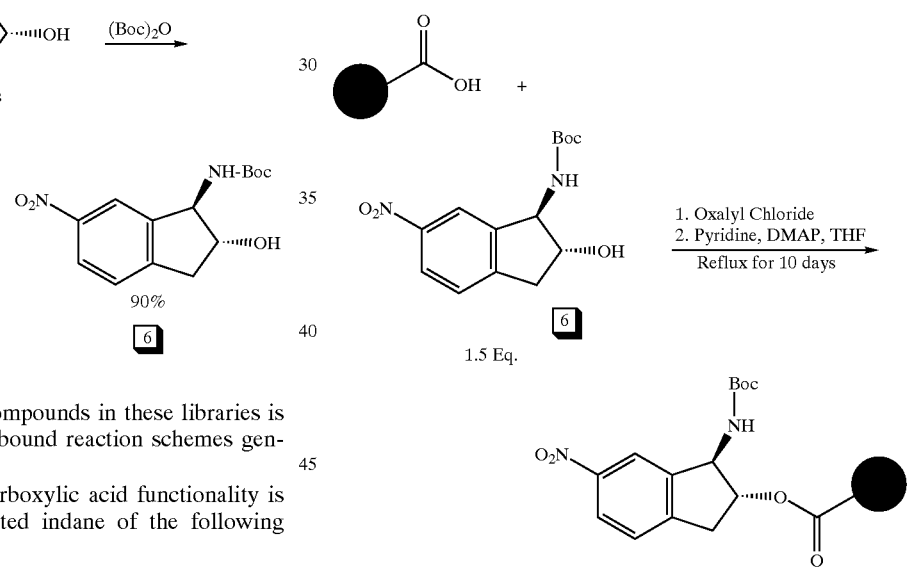

SOLID PHASE INDAN CHEMISTRY

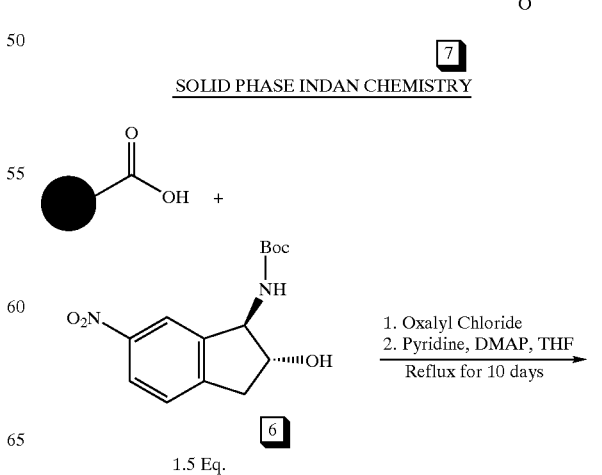

11
-continued
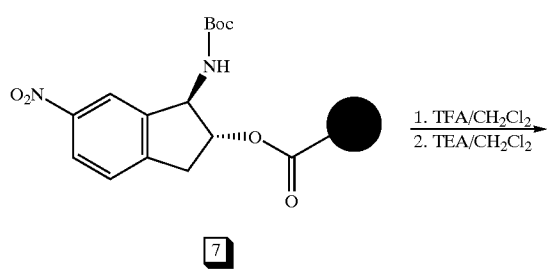
1. TFA/CH$_2$Cl$_2$
2. TEA/CH$_2$Cl$_2$
7
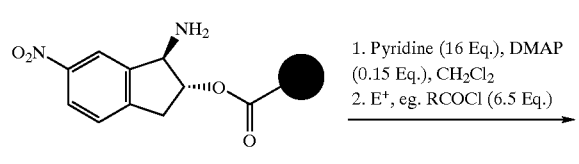
1. Pyridine (16 Eq.), DMAP (0.15 Eq.), CH$_2$Cl$_2$
2. E$^+$, eg. RCOCl (6.5 Eq.)
8
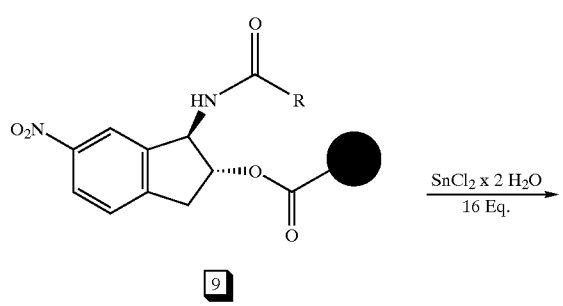
SnCl$_2$ x 2 H$_2$O
16 Eq.
9
12
-continued
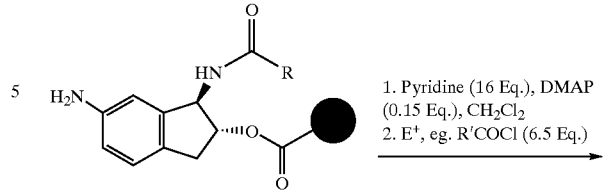
1. Pyridine (16 Eq.), DMAP (0.15 Eq.), CH$_2$Cl$_2$
2. E$^+$, eg. R'COCl (6.5 Eq.)
10
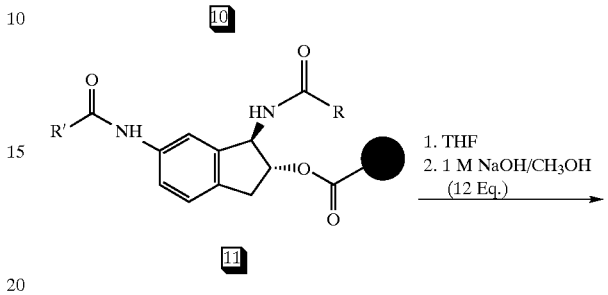
1. THF
2. 1 M NaOH/CH$_3$OH (12 Eq.)
11
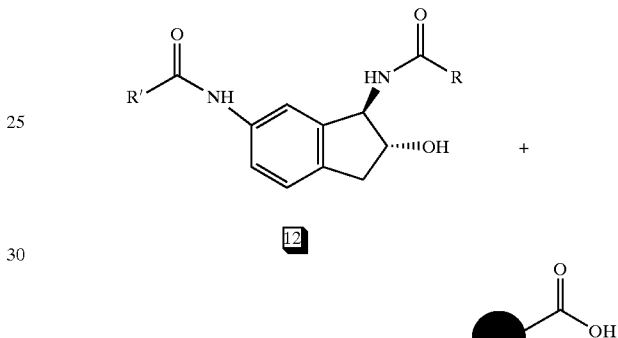
12
Alternatively, the scheme can proceed as follows for the formation of compounds of Formula V:
INDAN SCAFFOLD
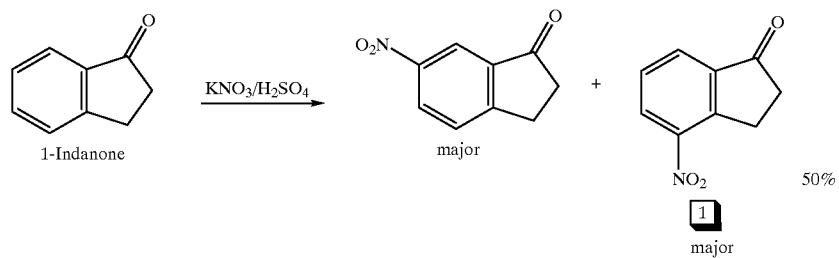
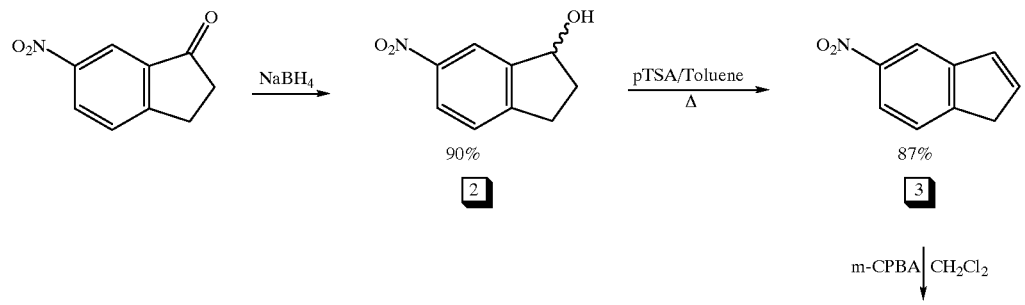
m-CPBA | CH$_2$Cl$_2$

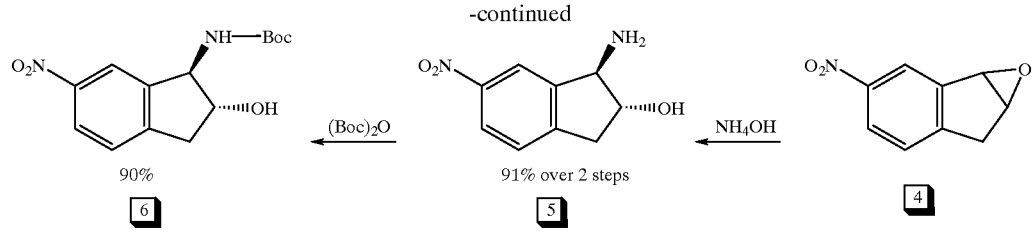
SOLID PHASE INDAN CHEMISTRY
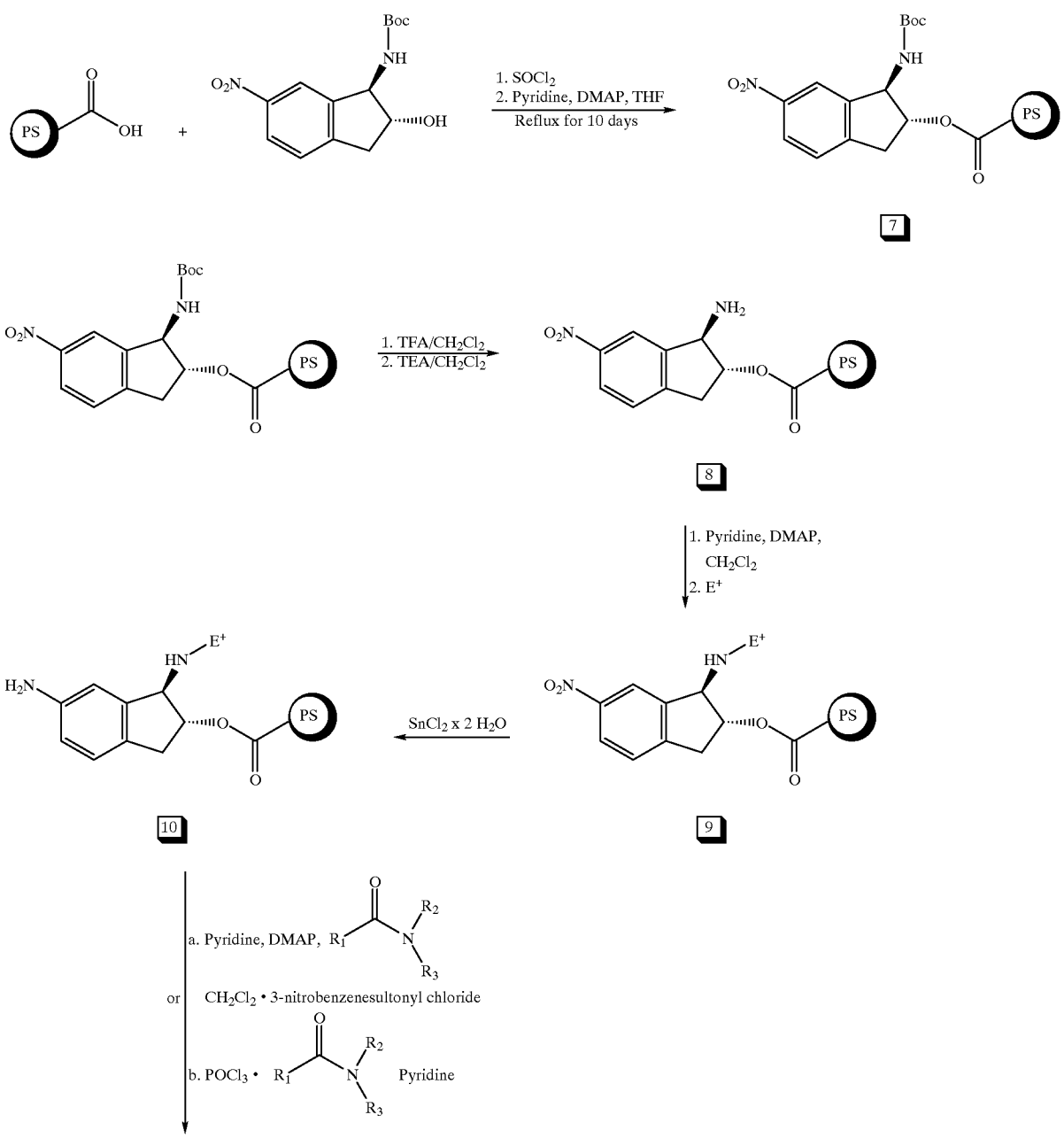

-continued

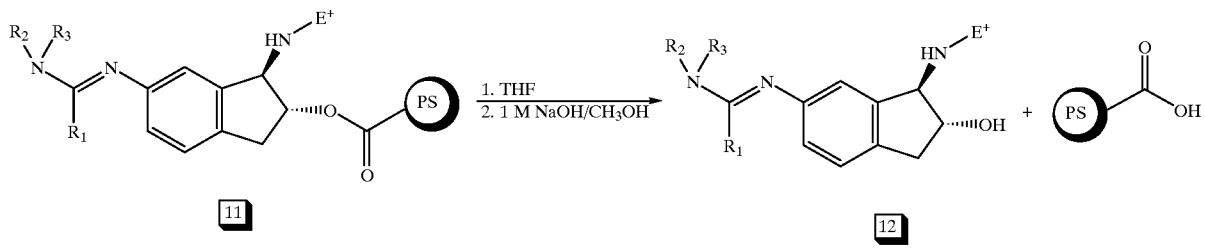

Multiple simultaneous synthesis may be performed by a variety of apparatus, such as that shown for multiple simultaneous synthesis U.S. Pat. No. 5,324,483; the disclosure of which is incorporated herein by reference.

The compounds of this invention can be prepared using the following general techniques. The skilled artisan will appreciate that there are alternative methods to obtain the desired compounds claimed herein.

Scheme 1

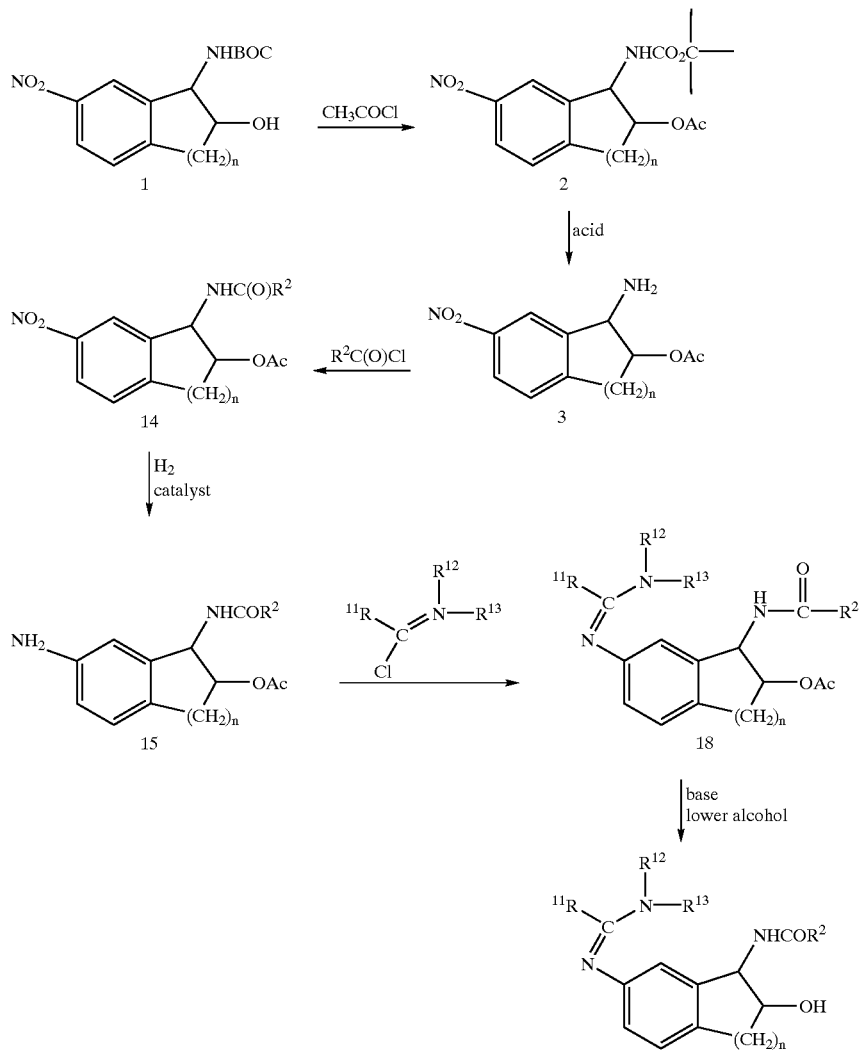

As illustrated by Scheme I, 1 which is commercially available or may be prepared by the skilled artisan using known methods, is dissolved in a mixture of pyridine, 4-dimethylaminopyridine and an inert organic solvent, wherein preferred inert organic solvents include but are not limited to solvents such as THF or $CH_2Cl_2$, as acetyl chlorideis added. The mixture may be treated with cold water and the organic layer separated. The organic solution is washed, the organic layer dried, and the solvent evaporated to give 2. A solution of 2 in THF or anther appropriate solvent is treated with a stream of dry HCl. The solution is treated with most preferredly cold saturated sodium bicarbonate, the organic phase was washed, dried and the solvent evaporated to give 3. A solution of 3 in a mixture of pyridine, 4-dimethylaminopyridine, and $CH_2Cl_2$ is treated with a solution of an arylsulfonyl chloride and the reaction stirred. The reaction is most preferredly poured into ice-water, the organic layer separated and consecutively washed. Preferred washes are with 1 N HCl and brine. The organics are dried and the solvent evaporated to give 14. A solution of 14 is treated with $SnCl_2$—$2\ H_2O$. The reaction mixture is preferredly poured into ice-water, the reaction made basic, and the mixture extracted. The organic extracts are washed, the solution dried, and the solvent evaporated 15. Alternatively, a solution of 14 in EtOAc or THF is treated with $H_2$ (about 60 psi) in the presence of a catalyst. Preferred catalysts are chosen from but not limited to the group consisting of $PtO_2$, Rainey-Ni, and Pd—C. The catalyst is removed and the solvent evaporated to give 15. A solution of 15 is treated with a solution of a chioroalkylene dialkylammonium chloride. It is noted here that the artisan should recognize that other reagents analagous to chloroalkylidene dialkylammonium chloride can also provide the desired compounds. The reaction was preferredly poured into ice-water, the organic layer separated and consecutively washed. Preferred washes are with saturated sodium bicarbonate and brine. The organics are dried and the solvent evaporated to give 18. A solution of 18 in base is stirred. The reaction mixture is preferredly poured into ice-water and extracted. The organic extracts are washed, dried, and the solvent evaporated to give the desired compound of this invention.

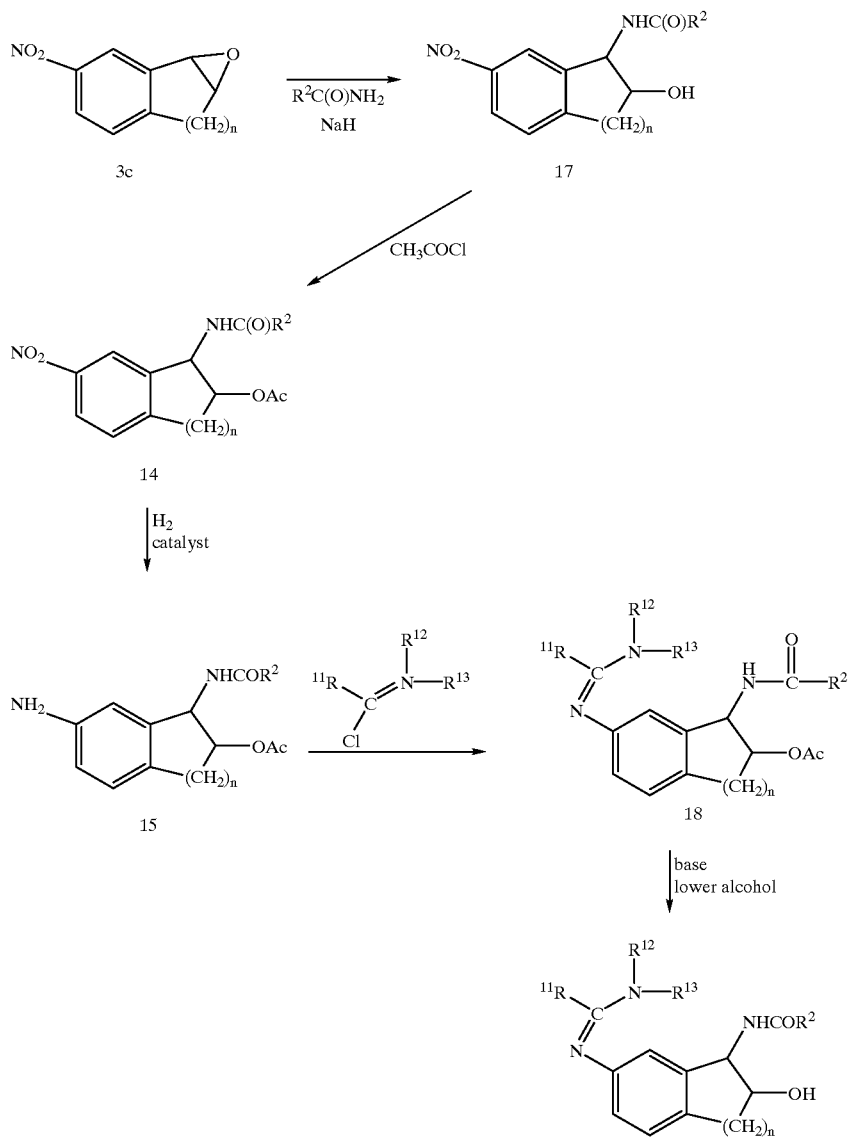

Scheme II

As illustrated by Scheme II, compounds of this invention can be prepared by a solution of a benzamide being treated with NaH and preferredly, the reaction mixture is stirred until gas evolution ceased. 1,2-Epoxy-6-nitroindane is added. Preferredly the 1,2-epoxy-6-nitroindane is added at about 60 C and stirred. The reaction is preferredly poured into ice-water and extracted. The organic extracts are washed, dried, and the solvent evaporated. The residue is chromatographed to obtain 17. A solution of 17 in a mixture of pyridine, 4-dimethylaminopyridine and an inert organic solvent, for example but not limited to solvents such as THF or $CH_2Cl_2$, as acetyl chloride is added. The reaction is preferredly treated with cold water and the organic layer separated. The organic solution is washed, dried, and the solvent evaporated to give 14. Processing of 14 as in Scheme I provides the desired compounds of this invention.

Scheme III

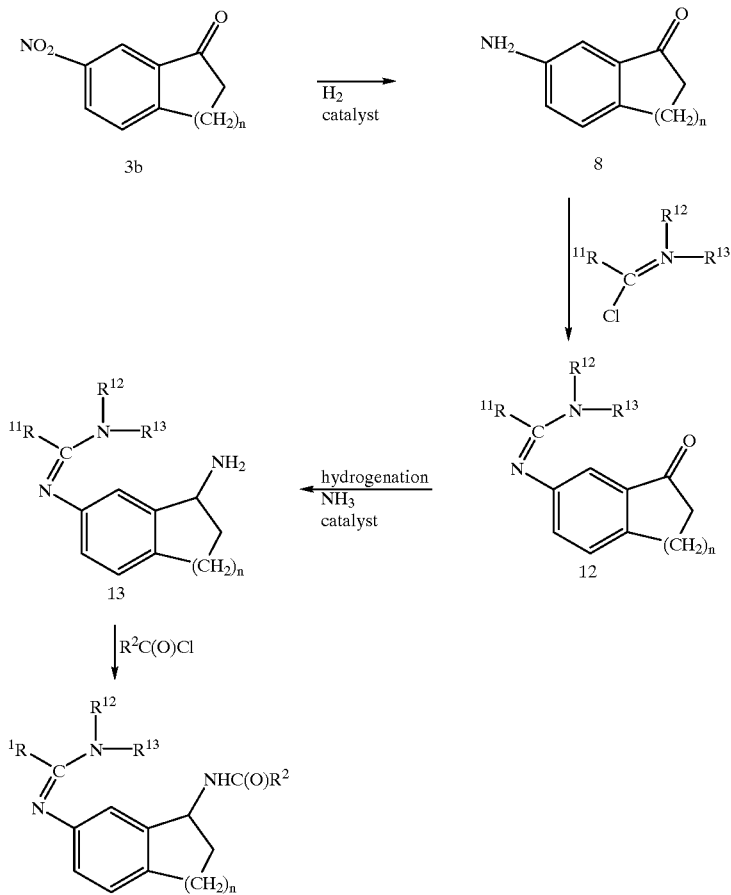

As illustrated by Scheme III, certain compounds of this invention can be prepared by a mixture of 6-nitroindan-1-one and a catalyst, which is preferredly, but not limited to one chosen from $PtO_2$, Rainey-Ni, and Pd—C in EtOH, is treated with hydrogen. The catalyst is removed and the solvent evaporated to give 8. A solution of 8 in a mixture of pyridine, 4-dimethylaminopyridine, and $CH_2Cl_2$ is treated with a solution of a chloroalkylidene dialkylammonium chloride and the reaction mixture is preferredly stirred. It is noted here that the artisan should recognize that other reagents analagous to chloroalkylidene dialkylammonium chloride can also provide the desired compounds. The reaction is preferredly poured into ice-water, the organic layer separated and consecutively washed. Preferred washes are with saturated sodium bicarbonate and brine. The organics are dried and the solvent evaporated to give 12. A solution of 12 in a mixture of lower alcohol and $NH_3$ is treated with hydrogen in the presence of a catalyst which is most preferredly, but not limited to, either Pd—C-sulfided or Pt—C sulfided. The catalyst is removed and the solvent evaporated to give 13. A solution of 13 in a mixture of pyridine, 4-dimethylaminopyridine, and CH$_2$Cl$_2$ is treated with a solution of an arylsulfonyl chloride. The reaction is preferredly poured into ice-water, the organic layer separated and consecutively washed. Preferred washes are with saturated sodium bicarbonate and brine. The organics are dried and the solvent evaporated to give the desired compound of this invention.

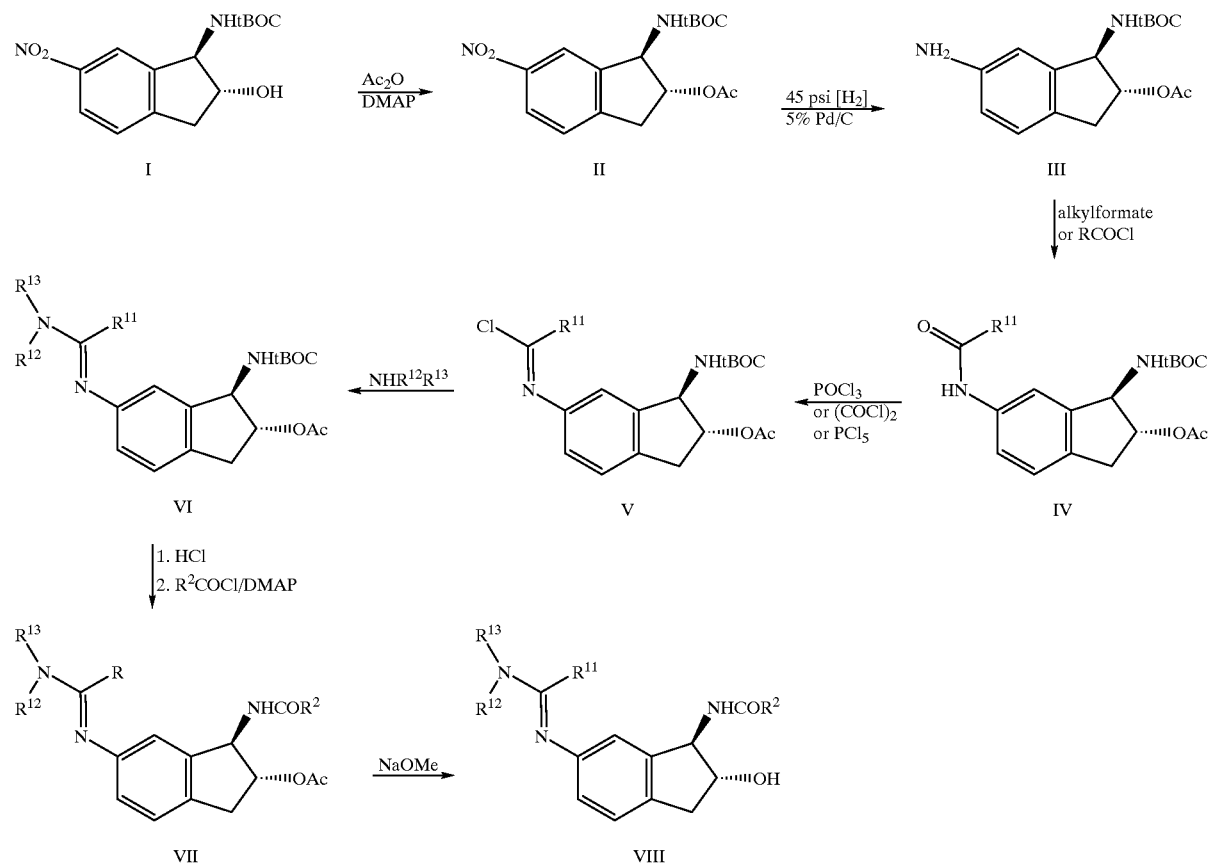

Step 1.

Protection of the 3-amino group of compound 5, preferably as a carbamate such as t-butyl carbamate, under standard conditions[1] provided compound 1 (also referred to as 6 supra.). Other similar protecting groups can be utilized in place of t-butyl carbamate. Carbamates are particularly preferred protecting groups for the synthesis described by Step 1.

[1] Greene and Wuts, Protecting Groups in Organic Chemistry,

Step 2.

Reduction of the nitro group may be accomplished using reagents such as SnCl$_2$, NaBH$_4$, or more preferably using metal-catalyzed hydrogenation.[2] Most preferably, Pd/C was used in EtOH at 50 psi and ambient temperature.

[2] Rylander, Hydrogenation

Step 3.

The amidine functionality of compounds 57–76 may be prepared from the amine by a variety of methods using reagents such as Gold's reagent. Most preferably the dimethyl amidine was prepared using N,N-dimethylformamide dimethyl acetal under standard conditions.[3]

[3] Patel amidine series and Meyers paper and ref. 4.

Step 4.

The amidine may be exchanged in the presence of higher boiling amines such as pyrollidine, piperidine, morpholine, or benzyl amine to provide compounds 6–56 and 77–105.[4]

[4] Transainidination reaction references.

Step 5.

The t-butyl carbamate protecting group was removed under standard conditions (ref 1) using cold trifluoroacetic acid.

Step 6.

The trifluoroacetate salt of the amine was reacted with a variety of acid chlorides in the presence of a base such as triethylamine at −10° C. to ambient temperature in a solvent such as methylene chloride to provide compounds VII.

Step 7.

The alcohol group of compounds 5–105 may be acylated or alkylated with reagents such as acetic anhydride in the presence of a base such as triethyl amine. The compounds of this invention can form acid addition salts with a wide variety of inorganic and organic acids. Typical acids which can be used include sulfuric, hydrochloric, hydrobromic, phosphoric, hypophosphoric, hydroiodic, sulfamic, citric, acetic, maleic, malic, succinic, tartaric, cinnamic, benzoic, ascorbic, mandelic, p-toluenesulfonic, benzenesulfonic, methanesulfonic, trifluoroacetic, hippuric and the like. The pharmaceutically acceptable acid addition salts of the compounds of this invention are especially preferred.

The compounds of the present invention are useful for modulating or blocking the M-1 receptor and can be useful for modulating or blocking a serotonin receptor. Certain of the present compounds are preferred for that use. Preferred compounds and embodiments of this invention are those having the following characteristics. The following preferred characteristics may be independently combined to provide further preferred embodiments of this invention:

A) $R^3$ is aryl;
B) $R^1$ is hydrogen;
C) $R^1$ is —OH;
D) $R^3$ is substituted phenyl having 3,4-dichloro substituents;
E) $R^2$ is substituted phenyl having 3,4-dichloro or meta trifluoromethyl substituents;
F) n is one;
G) the indane ring is saturated;
H) $R^3$ is bicycloaryl;
I) $R^3$ is substituted phenyl having a meta $NO_2$ substituent;
J) $R^3$ is $C_1$–$C_4$ alkyl;
K) $R^3$ is substituted $C_1$–$C_6$ alkyl wherein the terminal carbon of the alkyl chain is substituted with $CO_2R^4$ wherein $R^4$ is hydrogen, methyl, or ethyl;
L) $R^1$ is OH, n is 1 and the OH group is located at the 2 position of the ring;
M) a compound of this invention is used for treating psychosis;
N) A compound of Formula I:

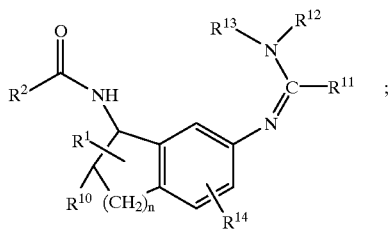

O) n is 1;
P) $R^2$ is substituted phenyl;
Q) A compound of Formula III;
R) A compound of Formula IV, wherein $R^{20}$ is a carbamate;
S) A compound of Formula I wherein $R^{12}$ and $R^{13}$ are independently $C_1$–$C_3$ alkyl;
T) A compound of Formula I wherein $R^{10}$ is hydrogen and $R^1$ is OH;
U) A compound of Formula I for treating a condition associated with modulation of an M4 muscarinic subtype receptor;
V) A compound of Formula I which acts as a muscarinic receptor agonist.
W) A compound of Formula V which acts as a muscarinic receptor agonist.

Further, the present invention contemplates both the cis and trans stereoisomers of the compounds of Formula I and Formula V. The trans configuration is preferred.

The present invention contemplates racemic mixtures as well as the substantially pure enantiomers of the compounds of Formula I and Formula V. The term "enantiomer" is used herein as commonly used in organic chemistry to denote a compound which rotates the plane of polarization. Thus, the "- enantiomer" rotates the plane of polarized light to the left, and contemplates the levorotary compound of Formula I and Formula V. The + and − enantiomers can be isolated using classical resolution techniques. One particularly useful reference which describes such methods is Jacques et. al. *Enantiomers, Racemates, And Resolutions* (John Wiley and Sons 1981). Appropriate resolution methods include direct crystallization, entrainment, and crystallization by optically active solvents. Chrisey, L. A. *Heterocycles*, 267, 30 (1990). A preferred resolution method is crystallization by an optically active acid or by chiral synthesis using the method of A. I. Meyers. Loewe, M. F. et al., *Tetrahedron Letters*, 3291, 26 (1985), Meyers, A. I. et al., *J. Am. Chem. Soc.* 4778, 110 (1988). Preferred optically active acids include camphorsulfonic and derivatives of tartaric acid.

The compounds of the present invention are known to form hydrates and solvateswith appropriate solvents. Preferred solvents for the preparation of solvate forms include water, alcohols, tetrahydrofuran, DMF, and DMSO. Preferred alcohols are methanol and ethanol. Other appropriate solvents may be selected based on the size of the solvent molecule. Small solvent molecules are preferred to facilitate the corresponding solvate formation. The solvate or hydrate is typically formed in the course of recrystallization or in the course of salt formation. One useful reference concerning solvates is Sykes, Peter, *A Guidebook to Mechanism in Organic Chemistry*, 56+, 6th Ed (1986, John Wiley & Sons, New York). As used herein, the term "solvate" includes hydrate forms, such as monohydrates and dihydrates.

The column chromatography procedures used standard flash chromotagraphy techniques. One well-known reference describing appropriate flash chromotagraphy techniques is Still, W. C. Kahn, and Mitra, *J. Org. Chem.* 1978, 43, 2932. Fractions containing product were generally evaporated under reduced vacuum to provide the product.

Optical rotations were obtained using methanol, pyridine, or other suitable solvent.

The hydrochloride salt of the particular compound was prepared by placing the free base into diethyl ether. While stirring this ether solution, a solution of HCl in diethyl ether was added dropwise until the solution became acidic. Alternatively, the ether solution was treated with dry HCl gas.

The maleate salt of the particular compound was prepared by placing the fiee base in ethyl acetate and treating with maleic acid. The precipitate formed was filtered and dried to provide the corresponding maleate salt of the free base.

I. Muscarinic Activity.

As used herein the term "malfunctioning of the muscarinic cholinergic system" shall have the meaning accepted by the skilled artisan. For example the term shall refer to, but is not in any way limited to, conditions such as glaucoma, psychosis, schizophrenia or schizophreniform conditions, depression, sleeping disorders, epilepsy, and gastrointestinal motility disorders. Other such conditions include Alzheimer's Disease and incontinence.

The pharmacological properties of the compounds of the invention can be illustrated by determining their capability to inhibit the specific binding of [3]H-Oxotremorine-M ([3]H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

[3]H-Oxo labels muscarinic receptor in the CNS (with a preference for agonist domains of the receptors). Three different sites are labeled by [3]H-Oxo. These sites have affinity of 1.8, 20 and 3000 nM, respectively. Using the present experimental conditions only the high and medium affinity sites are determined.

The inhibitory effects of compounds on $^3$H-oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 s in 10 mL 20 nM Hepes pH: 7.4, with an Ultra-Turrax homogenizer. The homogenizer is rinsed with 10 mL of buffer and the combined suspension centrifuged for 15 min. at 40,000×g. The pellet is washed three times with buffer. In each step the pellet is homogenized as before in 2×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 25 µL of test solution and 25 µL of $^3$H-Oxotremorine (1.0 nM, final concentration) mixed and incubated for 30 min. at 25° C. Non-specific binding is determined in triplicate using arecoline (1 µg/mL, final concentration) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non specific binding.

Test substances are dissolved in 10 mL water (if necessary heated on a steam-bath for less than 5 min.) at a concentration of 2.2 mg/mL. 25–75% inhibition of specific binding must be obtained before calculation of $IC_{50}$. The test value will be given as $IC_{50}$ (the concentration (nM) of the test substance which inhibits the specific binding of $^3$H-oxo by 50%).

$IC_{50}$=(applied test substance concentration)×$(C_x/C_o-C_x)$nM where $C_o$ is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$HPRZ (pirenzepine, [N-methyl-$^3$H]) binding to rat cerebral cortex membranes. Pirenzepine binds selectively to subtype of muscarinic receptors. Historically the type is named the M1-site, whereas pirenzepine sensitive site would be more appropriate. Although selective for $M_1$-sites pirenzepine also interact with $M_2$-sites.

All preparations are performed at 0–4° C. unless otherwise indicated. Fresh cortex (0.1–1 9) from male Wistar rats (150–200 g) is homogenized for 5–10 s in 10 mL 20 mM Hepes pH: 7.4, with an Ultra-Turrax homogenizer. The homogenizer is rinsed with 2×10 mL of buffer and the combined suspension centrifuged for 15 min. at 40,000×g. The pellet is washed three times with buffer. In each step the pellet is homogenized as before in 3×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 20 µL of test solution and 25 µL of $^3$HPRZ (1.0 nM, final conc.), mixed and incubated for 60 min. at 20° C. Non-specific binding is determined in triplicate using atropine (1.0 µg/mL, final conc.) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non-specific binding.

Test substances are dissolved in 10 mL water, at a concentration of 0.22 mg/mL. 25–75% inhibition of specific binding must be obtained before calculation of $IC_{50}$.

The test value will be given as $IC_{50}$ (the concentration (nM) of the test substance which inhibits the specific binding of $^3$HPRZ by 50%).

$IC_{50}$=(applied test substance concentration)×$(C_x/C_o-C_x)$nM where $C_o$ is specific binding in control assays and $C_x$ is the specific binding in the test assay. (The calculations assume normal mass-action kinetics).

Compounds of this invention showed particularly desirable activity using the muscarinic receptor assays. Most compounds were effective at an $IC_{50}$ concentration of less than 10 µMolar (no atropine). The muscarinic effect was confirmed by determining if the effect was blocked by atropine.

II. M4 muscarinic receptor binding assay

Cyclic AMP Accumulation in Pertussis Toxin-Treated CHO m4 Cells. CHO K1 cells transfected with human m4 receptors were grown to near confluency in T-150 flasks using Dulbecco's Modified Eagle Medium (DMEM) containing 10% fetal bovine serum. Cells were detached with 0.05% trypsin, 0.53 mM EDTA, and were suspended in medium containing 100 ng/ml pertussis toxin. Cells were plated at 30,000 cells per well into 96 well plates. Eighteen to twenty hours later the medium was removed and the cells were washed with serum-bee medium. Attached cells were incubated at 37 C for one hour after addition of 100 ml of serum free DMEM containing 1 mM 3-isobutyl-1-methylxanthine and 1 mM forskolin plus or minus drugs being tested. Incubations were terminated with 200 ml per well of serum free DMEM containing 0.3% triton-X-100. After stopping incubations the plates were allowed to sit for 20 minutes to extract cAMP and samples were then diluted 2.5-fold and were assayed using the scintillation proximity assay of Amersham (Arlington Heights, Ill.).

Representative results from the M4 assay are as follows

Stimulation of cyclic AMP production in CHO-m4 cells.

| Compound Number | % Maximum Stimulation Compared to Oxotremorine-M |
|---|---|
| 11 | 34 |
| 12 | 26 |
| 13 | <20 |
| 14 | 100 |
| 15 | 76 |
| 17 | 56 |
| 18 | 61 |
| 19 | <20 |
| 20 | 69 |
| 21 | 23 |
| 22 | <20 |
| 23 | <20 |
| 24 | 22 |
| 25 | 43 |
| 26 | <20 |
| 27 | <20 |
| 28 | <20 |
| 29 | <20 |
| 30 | <20 |
| 31 | 45 |
| 32 | <20 |
| 33 | 45 |
| 34 | 45 |
| 35 | 65 |
| 36 | <20 |
| 37 | 76 |
| 38 | <20 |
| 39 | 43 |
| 40 | 96 |
| 41 | <20 |
| 44 | 41 |
| 45 | <20 |

-continued

| Compound Number | % Maximum Stimulation Compared to Oxotremorine-M |
|---|---|
| 46 | 154 |
| 47 | <20 |
| 57 | 5 |
| 58 | 74 |
| 59 | 22 |
| 60 | 100 |
| 61 | 39 |
| 62 | 27 |
| 63 | 13 |
| 64 | 52 |
| 65 | 30 |
| 66 | 0 |
| 67 | 7 |
| 68 | 0 |
| 69 | 14 |
| 70 | 18 |
| 71 | 95 |
| 72 | 4 |
| 73 | 11 |
| 74 | 8 |
| 75 | 6 |
| 76 | 130 |
| 77 | 214 |
| 88 | 52 |
| 97 | 36 |
| 98 | 73 |

III. M1 Agonist Receptor Assay

Primary Assay:

CHO (Chinese hamster transfected with the human m1 receptor (CHO-m1) were grown to confluency in flasks using Dulbecco's Modified Eagle Medium (DMEM) containing 10% fetal bovine serum. Cells were detached with 0.05% trypsin, 0.53 mM EDTA. Cells were collected after centrifugation in a Beckman centrifuge at 1000 rpm for 10 minutes, diluted with culture medium (400,000 cells/ml) Aarachidonic acid was added to the cell solution at a 1:2000 ratio of a 1 mCi/ml stock and cells were plated at 40,000 cells per well into 96 well plates and incubated for 18 to 24 hours at 37 C and 5% $CO_2$. Following the incubation, the medium was removed and the cells were washed with D-ME medium containing 2 mg/mL of fatty acid free BSA (250 L/well). The test compound of interest was diluted in D-ME-BSA and added to each well (150 L/well), incubated for 120 minutes at 37 C in 5% $CO_2$. 80 L of supernatant was transferred to Wallac 96 well plates containing 110 L/well of Supermax scintillation cocktail at pH 9.0. Plates were counted in a Wallae microbeta counter.

Representative results from the m1 primary assay are as follows:

| Compound Number | Screening Table Max. % activity @ 5 $\mu$M |
|---|---|
| 118 | 57.4 |
| 119 | 66.4 |
| 120 | 92.5 |
| 121 | 45.4 |
| 122 | 80.9 |
| 123 | 76.7 |
| 124 | 82.2 |
| 125 | 114.0 |
| 126 | 102.2 |
| 127 | 69.8 |
| 134 | 75.9 |

Secondary m1 assay:

The pharmacological properties of the compounds of the invention can be illustrated by determining their capability to inhibit the specific binding of 3H-Oxotremorine-M (3H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

3H-Oxo labels muscarinic receptor in the CNS (with a preference for agonist domains of the receptors). Three different sites are labeled by 3H-Oxo. These sites have affinity of 1.8, 20 and 3000 nM, respectively. Using the present experimental conditions only the high and medium affinity sites are determined.

The inhibitory effects of compounds on 3H-oxo binding reflects the affinity for muscarinic acetylcholine receptors.

All preparations are performed at 0–4$_i$C unless otherwise indicated. Fresh cortex (0.1–1 g) from male Wistar rats (150–250 g) is homogenized for 5–10 seconds in 10 mL 20 nM Hepes pH: 7.4, with an Ultra-Turrax homogenizer. The homogenizer is rinsed with 10 mL of buffer and the combined suspension centrifuged for 15 min. at 40,000×g. The pellet is washed three times with buffer. In each step the pellet is homogenized as before in 2×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 ML is added 25 $\mu$L of test solution and 25 $\mu$L of 3H-Oxotremorine (1.0 nM, final concentration) mixed and incubated for 30 min. at 25 $_i$C. Non-specific binding is determined in triplicate using arecoline (1 $\mu$g/mL, final concentration) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non specific binding.

Test substances are dissolved in 10 mL water (if necessary heated on a steam-bath for less than 5 min.) at a concentration of 2.2 mg/mL. 25–75% inhibition of specific binding must be obtained before calculation of IC50. The test value will be given as IC50 (the concentration (nM) of the test substance which inhibits the specific binding of 3H-oxo by 50%).

IC50=(applied test substance concentration)×ⒸxCo−Cx)nM where Co is specific binding in control assays and Cx is the specific binding in the test assay. (The calculations assume normal mass-action kinetics).

Furthermore the pharmacological properties of the compounds of the invention can also be illustrated by determining their capability to inhibit 3HPRZ (pirenzepine, [N-methyl-3H]) binding to rat cerebral cortex membranes.

Pirenzepine binds selectively to subtype of muscarinic receptors. Historically the type is named the M1-site, whereas pirenzepine sensitive site would be more appropriate. Although selective for M1-sites pirenzepine also interact with M2-sites.

All preparations are performed at 0–4$_i$C unless otherwise indicated. Fresh cortex (0.1–1 9) from male Wistar rats (150–200 g) is homogenized for 5–10 s in 10 mL 20 mM Hepes pH: 7.4, with an Ultra-Turrax homogenizer. The homogenizer is rinsed with 2×10 mL of buffer and the combined suspension centrifuged for 15 min. at 40,000×g. The pellet is washed three times with buffer. In each step the pellet is homogenized as before in 3×10 mL of buffer and centrifuged for 10 min. at 40,000×g.

The final pellet is homogenized in 20 mM Hepes pH: 7.4 (100 mL per g of original tissue) and used for binding assay.

Aliquots of 0.5 mL is added 20 μl of test solution and 25 μL of 3HPRZ (1.0 nM, final conc.), mixed and incubated for 60 min. at 20,C. Non-specific binding is determined in triplicate using atropine (1 μg/mL, final conc.) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non-specific binding.

Test substances are dissolved in 10 mL water, at a concentration of 0.22 mg/mL. 25–75% inhibition of specific binding must be obtained before calculation of IC50.

The test value will be given as IC50 (the concentration (nM) of the test substance which inhibits the specific binding of 3HPRZ by 50%).

IC50=(applied test substance concentration)×ⓒx/Co–Cx)nM where Co is specific binding in control assays and Cx is the specific binding in the test assay. (The calculations assume normal mass-action kinetics).

Representative results from the ml secondary assay are as follows:

| | Assay | |
|---|---|---|
| Compound Number | Pl stim. A9L-m1 % Max of carbachol | ED-50 Pl stim A9L-m1, nm |
| 128 | 59.2 | 95.3 |
| 129 | 42 | 41.3 |
| 130 | 64 | 9.2 |
| 131 | 70.5 | 43.6 |
| 132 | 59 | 183 |
| 133 | 40 | 190 |

IV. Psychosis Studies.

The antipsychotic activity of the presently claimed compounds can be demonstrated in models using well-established procedures. For example the compounds are studied to determine if they antagonize apomorphine-induced climbing behavioral and hypothermia in mice (Moore, N. A. et al. Psychophannacology 94 (2), 263–266 (1988), and 96, 539 (1988)) which measures the ability of the compound to prevent the disruption of climbing response produced by 24 hour pre-treatment with N-ethoxycarbonyl-2-ethoxy-1,2-dihydroquinoline (EEDQ), a dopamine receptor inactivating agent (Meller et al. Central D1 doparnine receptors, Plenum Press, 1988).and/or inhibite a conditioned avoidance response in rats ($ED_{50}$ 4–7 mg/kg).

The conflict procedure used is based on the method of Geller and Seifter, *Psychopharmacolopia* 1: 482–492, (1960). Rats are trained on a multiple schedule consisting of three components. Individual components are as follows: 1) for 9 minutes, lever pressing was reinforced on a variable interval 30 second schedule (VI 30, reward). This period is signaled by illumination of the house light alone. 2) During the following 3-minute period, lever presses are recorded but had no programmed consequence (time-out). 3) Lever pressing is reinforced according to a fixed ratio 10 second food presentation (FR10) for 3 minutes; however, each reinforced response is accompanied by an electric current (0.5 mA) being applied to the grid floor for 500 msec (conflict). This component is signaled by illumination of the houselight and three cue lights on the front panel. This sequence of three components (reward/time-out/conflict) are presented twice in the same order during the daily 30 minute session. Animals are given extensive training on this schedule until the following criteria had been satisfied: 1) rates of responding during the individual VI30 components do not differ by more than 10%; 2) rates of responding during time-out and conflict are less than 10% of the rate during the VI component; and 3) the above criteria are satisfied for a period of five days.

After the training procedure, drug testing is initiated. During this period, the animals are dosed orally with either test compounds or vehicle in a randomized order 60 minutes before testing. At least two drug-free training days occur between test sessions. This test indicates that the compound has anxiolytic properties which are not observed with typical antipsychotic agents. Spealman et al., *J. Pharmacol. Exp. Ther.* 212:435–440, 1980.

Further, the pharmacological profile of the claimed compounds is desirable for use in the treatment of other conditions which are related to the mediation of a muscarinic receptor. Such conditions include for example, Alzheimer's Disease, glaucoma, irritable bowel syndrome, bladder dysfunction and incontinence, treatment of pain, analgesia, Huntington's Disease, epilepsy, Parkinson's Disease, anxiety, and other psychotic conditions as described in the DSM-IV.

While it is possible to administer a compound of the invention directly without any formulation, the compounds are preferably employed in the form of a pharmaceutical formulation comprising a pharmaceutically acceptable excipient and at least one compound of the invention. Such compositions contain from about 0.1 percent by weight to about 90.0 percent by weight of a present compound. As such, the present invention also provides pharmaceutical formulations comprising a compound of the invention and a pharmaceutically acceptable excipient therefor. In making the compositions of the present invention, the active ingredient is usually mixed with an excipient which can be a carrier, or a diluent or be diluted by a carrier, or enclosed within a carrier which can be in the form of a capsule, sachet, paper or other container. When the carrier serves as a diluent, it can be a solid, semi-solid, or liquid material which acts as a vehicle, excipient, or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

The compounds of the invention may be delivered transdermally, if desired. Transdermal permeation enhancers and delivery systems, including patches and the like, are well known to the skilled artisan.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxy-benzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For oral administration, a compound of this invention ideally can be admixed with carriers and diluents and molded into tablets or enclosed in gelatin capsules. The compositions are preferably formulated in a unit dosage form, each dosage containing from about 0.1 to about 500 mg or more, usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical carrier.

In order to more fully illustrate the operation of this invention, the following formulation examples are provided. The examples are illustrative only, and are not intended to limit the scope of the invention. The formulations may employ as active compounds any of the compounds of the present invention.

Formulation 1

Hard gelatin capsules are prepared using the following ingredients:

|  | Concentration | |
|---|---|---|
|  | Amount Per Capsule | by Weight (percent) |
| A compound of this invention | 250 mg | 55.0 |
| starch dried | 200 mg | 43.0 |
| magnesium stearate | 10 mg | 2.0 |
|  | 460 mg | 100.0 |

The above ingredients are mixed and filled into hard gelatin capsules in 460 mg quantities.

Formulation 2

Capsules each containing 20 mg of medicament are made as follows:

|  | Concentration | |
|---|---|---|
|  | Amount Per Capsule | by Weight (percent) |
| A compound of this invention | 20 mg | 10.0 |
| starch | 89 mg | 44.5 |
| microcrystalline cellulose | 89 mg | 44.5 |
| magnesium stearate | 2 mg | 1.0 |
|  | 200 mg | 100.0 mg |

The active ingredient, cellulose, starch, and magnesium stearate are blended, passed through a No. 45 mesh U.S. sieve and filled into a hard gelatin capsule.

Formulation 3

Capsules each containing 100 mg of medicament are made as follows:

|  | Concentration | |
|---|---|---|
|  | Amount Per Capsule | by Weight (percent) |
| a compound of this invention | 100 mg | 30.00 |
| polyoxyethylene sorbitan monooleate | 50 mg | 0.02 |
| starch powder | 250 mg | 69.98 |
|  | 350.05 mg | 100.00 |

The above ingredients are thoroughly mixed and placed in an empty gelatin capsule.

Formulation 4

Tablets containing 10 mg of active ingredient are made as follows:

|  | Concentration | |
|---|---|---|
|  | Amount Per Capsule | by Weight (percent) |
| a compound of this invention | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |
| magnesium stearate | 0.5 mg | 0.5 |
| talc | 1 mg | 1.0 |
|  | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

Formulation 5

A tablet formulation may be prepared using the ingredients below:

|  | Amount Per Capsule | Concentration by Weight (percent) |
|---|---|---|
| A compound of this invention | 250 mg | 38.0 |
| microcrystalline cellulose | 400 mg | 60.0 |
| silicon dioxide fumed | 10 mg | 1.5 |
| stearic acid | 5 mg | 0.5 |
|  | 665 mg | 100.0 |

The components are blended and compressed to form tablets each weighing 665 mg.

Formulation 6

Suspensions each containing 5 mg of medicament per 5 ml dose are as follows:

|  | per 5 ml of suspension |
|---|---|
| A compound of this invention | 5 mg |
| sodium carboxymethyl cellulose | 50 mg |
| syrup | 1.25 ml |
| benzoic acid solution | 0.10 ml |
| flavor | q.v. |
| color | q.v. |
| water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

|  | Concentration by Weight (percent) |
|---|---|
| A compound of this invention | 0.25 |
| ethanol | 29.75 |
| Propellant 22 (chlorodifluoromethane) | 70.00 |
|  | 100.00 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

The following Examples further illustrate certain of the compounds of the present invention, and methods for their preparation. The examples are illustrative only, and are not intended to limit the scope of the invention.

Preparation 1

Indane compounds are formed on a solid polymer support by the a series of process steps illustrated by the following 12 steps which are presented Preparation 1, Example 1 and Example 2, this process is further illustrated by Scheme IA, supra.

Steps 1–4 of Synthesis of Scheme IA.

1. To a solution of 1-indanone (25 g, 0.189 mol) in concentrated $H_2SO_4$ (84 ml) at 0° C. was added a solution of $KNO_3$ (8.33 g, 0.0824 mol) in $H_2SO_4$ (40 ml) as to maintain an internal temperature below 15° C. After stirring at 0° C. for 1 hr., the reaction mixture was poured into crushed ice and stirred vigorously for 30 min. The suspension was then filtered, air dried, and purified by LC (5% ethyl acetate/toluene) to provide $1^a$ (18.90 g, 56%) as a pale yellow solid.

2. A solution of $1^a$ (18.90 g, 0.107 mol) in methanol (300 ml) was cooled to 0° C. and $NaBH_4$ (4.04 g.0. 107 mol) was added in several small portions. The reaction was then stirred overnight at 25° C. The solution was quenched at 0° C. with methanolic HCl (200 ml), concentrated under reduced pressure, redissolved in $CH_2Cl_2$, washed with $H_2O$, and the organic layer reconcentrated to provide the crude alcohol as a brown solid.

3. To a solution of crude alcohol in toluene (300 ml) was added a catalytic amount of p-toluenesulfonic acid and the reaction was refluxed for 1 hr. using a Dean Stark trap to remove the $H_2O$. The organic layer was washed with sat'd. $NaHCO_3$ (3×200 ml), dried over $MgSO_4$, solvent removed under vacuum, and the product recrystallized from methanol to afford $3^a$ (13.41 g, 78% over two steps) as a tan solid.

4. To a solution of $3^a$ (10.53 g, 0.0653 mol) in dichloromethane (350 ml ) at 0° C. was added mCPBA (29 g, 0.0924 mol) in small amounts over the course of 1 hr. After stirring overnight at 25° C., the mixture was washed with sat'd $Na_2SO_3$ (2×200 ml), sat'd $NaHCO_3$ (2×200 ml), filtered through a cotton plug, and concentrated under vacuum. The product shall be referred to as $4^a$.

EXAMPLE 1

Step 5 of Synthesis of Scheme IA

5. A suspension of $4^a$ in concentrated $NH_4OH$ (250 ml) was heated overnight in an oil bath at 45° C. The next day $H_2O$ was added and the basic aqueous layer was sat'd. with NaCl. The cloudy reaction mixture was extracted with TBF until no more product could be seen by TLC. Organic layers were combined, dried over $MgSO_4$, concentrated, and recrystallized from ethyl acetate to give $5^a$ (11.54 g, 91% over two steps) as a fluffy tan solid. m.p. 148–150° C.

EXAMPLE 2

Step 6 of Synthesis of Scheme IA

6. To a solution of $5^a$ (8.34 g, 0.0429 mol) in THF (200 ml) was added a solution of di-tert-butyldicarbonate (11.25 g, 0.0515 mol) in TBF (50 ml). After stirring 1 hr. at 25° C., the solvent was removed under reduced pressure and the resulting solid was recrystallized from ethyl acetate to afford $6^a$ (11.37 g, 90%) as a white solid.

Step 7 of synthesis of Scheme IA

7. Under an $N_2$ atmosphere a 3 L three-necked round bottomed flask equipped with an overhead stirrer and addition final was charged with carboxylated polystyrene resin (70 g, 2.77 mmol $CO_2H$/g resin), anhydrous dichloromethane (1000 ml), and anhydrous DMF (10 ml). Next, oxalyl chloride (50.75 ml, 0.582 mol) was added via a slow dropwise addition from an addition funnel. After refluxing overnight under $N_2$, the solvent was removed under vacuum using a gas dispersion tube. The resin was subsequently washed with anhydrous dichloromethane (3×500 ml). Once the last wash was complete, the resin was dried under vacuum for 2–3 hrs. At this time, the polymer was resuspended in dry THF (1000 ml) followed by the addition of dry pyridine (314 ml, 3.88 mol), DMAP (11.85 g, 0.0970 mol), and 6 (85.62 g, 0.291 mol). The mixture was refluxed for 10 days under an inert atmosphere. The solvent was removed by vacuum filtration and the resin was washed with THF (3×300 ml), $CH_2Cl_2$ (3×300 ml), and dried overnight in a vacuum oven to provide $7^a$ (122.18 g) as a tan resin.

EXAMPLE 3

Step 8–12 of total synthesis Scheme IA

8. Into a round bottomed flask equipped with a stir bar was placed $7^a$ (28 mg, 0.02827 mmol), 0.500 ml dichloromethane, and TFA (0.109 ml, 0.14135 mmol).

The reaction mixture was stirred at 25° C. overnight, resin collected by filtration, resuspended in 10% TEA/CH$_2$Cl$_2$, stirred for 15 min., filtered again, and finally washed with dichloromethane to afford 8$^a$.

9. Into a 10 ml round bottomed flask was placed 7$^a$ (0.02827 mmol) followed by 0.5 ml of a solution of pyridine (0.03659 ml, 0.4524 mmol) and DMAP (0.518 mg, 0.004241 mmol) in dichloromethane. Next, a 1M solution of an electrophile in dichloromethane (0.1838 ml, 0.1838 mmol) was added and the resulting mixture was stirred overnight at 25° C. At this time the solvent was removed by vacuum filtration and the resin was washed with CH$_2$Cl$_2$, DMF, methanol, DMF, methanol, and CH$_2$Cl$_2$. This product is referred to as 9$^a$.

10. To a solution of 9$^a$ (0.02827 mmol) in DMF (0.625 ml) was added SnCl$_2$×2 H$_2$O (102 mg, 0.4524 mmol). Upon stirring at 25° C. for 48 hrs, the resin was isolated by filtration and washed with CH$_2$Cl$_2$, DMF, methanol, DMF, methanol, and CH$_2$Cl$_2$ to give 10$^a$.

11. Into a 10 ml round bottomed flask was placed 10$^a$ (0.02827 mmol) followed by 0.5 ml of a solution of pyridine (0.03659 ml, 0.4524 mmol) and DMAP (0.518 mg, 0.004241 mmol) in dichloromethane. Next, a 1M solution of an electrophile in dichloromethane (0.1838 ml, 0.1838 mmol) was added and the resulting mixture was stirred overnight at 25° C. At this time the solvent was removed by vacuum filtration and the resin was washed with CH$_2$Cl$_2$, DMF, methanol, DMF, methanol, and CH$_2$Cl$_2$ to give 11$^a$.

12. To a flask containing 11$^a$ (0.02827 mmol) was added a 1M solution of NaOH in methanol (.375 ml, 0.375 mmol) and THF (0.400 ml). After overnight stirring at 25° C., the reaction was neutralized with 4M HCl in methanol (0.100 ml, 0.400 mmol), resin filtered, and the filtate was concentrated under reduced pressure to provide 12$^a$.

EXAMPLE 3a

Steps 10–12 of alternative synthesis Scheme.

10. To a solution of 9$^a$ (0.02827 mmol) in 1-methyl-2-pyrrolidinone (0.625 ml) was added SnCl$_2$×2 H$_2$O (102 mg, 0.4524 mmol). Upon stirring at 25° C. for 48 hrs, the resin was isolated by filtration and washed with CH$_2$Cl$_2$ to give 10$^a$.

11. (a) Into a 10 ml round bottomed flask was placed 10$^a$ (0.02827 mmol) followed by 0.5 ml of a solution of pyridine (0.03659 ml, 0.4524 mmol), an amide or formamide (0.5654 mols), and DMAP (0.518 mg, 0.004241 mmol) in dichloromethane. Next, a 1 M solution of 3-nitrobenzenesulfonyl chloride in dichloromethane (0.1838 ml, 0.1838 mmol) was added and the resulting mixture was stirred overnight at 25°. At this time the solvent was removed by vacuum filtration and the resin was washed with CH$_2$Cl$_2$, DMF, methanol, DMF, methanol, and CH$_2$Cl$_2$ to give 11$^a$; or (b) To a solution of an amide or formamide (0.53g, 5.4 mmols) in 10 ml dry Dichloromethane was added POCl$_3$ (0.25g, 1.62 mmols) and the resulting solution was stirred at room temperature for 1 hr. This was then cannulated into a solution of indan aniline resin (0.250 g, 0.27 mmols) and pyridine (0.43 g, 5.4 mmols) in 10 ml dry dichloromethane. After overnight stirring at room temperature, the resin was filtered, washed with CH$_2$Cl$_2$, Ch$_3$OH, CH$_2$Dl$_2$ and dried under reduced pressure.

12. To a flask containing 11$^a$ (0.02827 mmol) was added a 1 M solution of NaOH in methanol (0.375 mmol) and THF (0.400 ml). After overnight stirring at 25° C., the reaction was neutralized with 4M HCl in methanol (0.100 ml, 0.400 mmol), resin filtered, and the filtrate was concentrated under reduced pressure to provide 12$^a$.

EXAMPLE 4

A 3 gallon stainless steel hydrogenation reactor was charged with 2.79 g (5% wt. load) of 5% Pd/C under a nitrogen purge. The catalyst was then wetted with toluene (25 mL). To this mixture was added a solution of 1 (55.39 g (0.188 mol) in 3A-EtOH (6 L). After purging the reactor with nitrogen, the reaction vessel was pressurized to 45 psi with hydrogen and stirred at room temperature for 4.5 h. TLC (Silica, 90/10 CH$_2$Cl$_2$/MeOH+1% NH$_4$OH) indicated the reaction was complete. The mixture was filtered through Hi-Flo and the filter cake rinsed with CH$_2$Cl$_2$ (2 L). The filtrate was transferred to a 12 L Buchii flask and concentrated in vacuo to afford 2 (47.79 g, 96%) as a white solid.

To a solution of 2 (5.0 g, 0.089 mol) in MeOH (50 mL) was added dimethylformamide-dimethylacetal (3.77 mL, 0.028 mol). After stirring at reflux for 1 h, a second aliquot of dimethylformamide-dimethyl acetal (3.77 mL, 0.028 mol) was added and reflux continued for another 1.5 h. TLC (Silica, 90/10 ethyl acetate/hexanes+2% Et$_3$N) indicated the reaction was complete. The mixture was cooled to room temperature and concentrated to a thick oil. The crude product was dissolved in CH$_2$Cl$_2$ (100 mL), washed with 1×25 mL D. I. H$_2$O, 2×50 mL 5% NaHCO$_3$, and dried over Na$_2$SO$_4$. Concentration in vacuo afforded 3 (6.17 g, 96%) as a light tan foam.

A solution of 3 (1.66 g, 0.0049 mol) in neat pyrrolidine (15 mL) was treated with 5 mg of (NH$_4$)$_2$SO$_4$ and heated to 80 C in an oil bath. After 4 hrs at 80 C, a small aliquot of the reaction mixture was removed, stripped to dryness and analyzed by N (CDCl$_3$, 500 MHz). Observation of a new amidine-H signal at 7.78 ppm with no signal remaining at 7.52 ppm indicated the reaction was complete. The mixture was concentrated to remove the excess pyrrolidine. The resulting crude oil was dissolved in CH$_2$Cl$_2$ (50 mL), washed with 1×25 mL H$_2$O, 1×25 mL 5% NaHCO$_3$, and 1×25 mL brine, then dried over Na$_2$SO$_4$. Concentration in vacuo afforded 4 as a tan foam (1.70 g, 95%).

EXAMPLE 5

Compound 4 (1.49 g, 0.0041 mol) was dissolved in cold (−5 C) trifluoroacetic acid (15 mL) and stirred at −5 C to −10 C for 15 minutes. TLC (Silica, 90/10 CH$_2$Cl$_2$/MeOH+1% NH$_4$OH) indicated the reaction was complete. The mixture was concentrated in vacuo to remove excess trifluoroacetic acid. The crude oil was dissolved in 2B-EtOH (4 mL) and treated with the dropwise addition of diethyl ether (30 mL). The resulting precipitate was filtered, washed with diethyl ether (15 mL) and dried under vacuum at 40 C. Compound 5 (1.70 g, 87%) was recovered as a white solid.

EXAMPLES 6–105

Examples 6 through 105 were prepared using substantially the procedure described as follows, using the corresponding reagents to provide the desired compound: Compound 5 (106 mg, 0.000224 mol) was suspended in CH$_2$Cl$_2$ (3.3 mL), cooled to 0 C and treated with Et$_3$N (0.09 mL, 0.000894 mol). The resulting solution was treated with benzoyl chloride (31 mL, 0.000268 mol) and the mixture stirred for 0.5 h. With TLC (Silica, 90/10 CH$_2$Cl$_2$/MeOH+ 1% NH$_4$OH) showing the reaction to be complete, the mixture was diluted with CH$_2$Cl$_2$ (2.5 mL) and quenched with H$_2$O (2.5 mL). The organic layer was washed with 1×5 mL H$_2$O, 3×2.5 mL 5% NaHCO$_3$, and 1×2.5 mL brine. After drying over Na$_2$SO$_4$, the mixture was concentrated in vacuo to afford 6 (76 mg, 97%) as a white foam.

EXAMPLES 6–105

Examples 6–105 are presented in the following table. The "Comp.#" corresponds to both the compound number and example number.

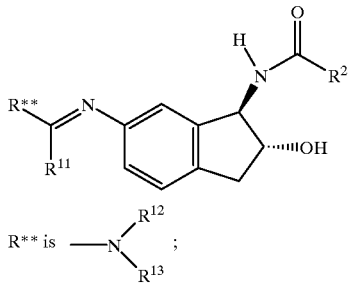

wherein R$^2$, R$^{11}$, R$^{12}$, and R$^{13}$ are defined as described supra.

| Comp. # | R** | R$^{11}$ | R$^2$ | Electrospray Ionization M. S. (M + 1) |
|---|---|---|---|---|
| 6 | 1-Pyrrolidine | H | Phenyl | 350 |
| 7 | 1-Pyrrolidine | H | 3,5 di(trifluoromethyl)-phenyl | 486 |
| 8 | 1-Pyrrolidine | H | 4-Butoxy-Phenyl | 422 |
| 9 | 1-Pyrrolidine | H | Cyclopentyl | 342 |
| 10 | 1-Pyrrolidine | H | 6-Chloro-3-Pyridinyl | 385 |
| 11 | 1-Pyrrolidine | H | Cyclohexyl | 356 |
| 12 | 1-Pyrrolidine | H | 2-Chloro-3-Pyridinyl | 385 |
| 13 | 1-Pyrrolidine | H | 4-Cyano-Phenyl | 375 |
| 14 | 1-Pyrrolidine | H | 3,5 dichlorophenyl | 419 |
| 15 | 1-Pyrrolidine | H | 1-Napthyl | 400 |
| 16 | 1-Pyrrolidine | H | 4-Ethylphenyl | 378 |
| 17 | 1-Pyrrolidine | H | 2-Napthyl | 400 |
| 18 | 1-Pyrrolidine | H | 4-Trifluoromethyl-Phenyl | 418 |
| 19 | 1-Pyrrolidine | H | Trifluoromethyl | 342 |
| 20 | 1-Pyrrolidine | H | 2-Chloro-4-Nitro-Phenyl | 429 |
| 21 | 1-Pyrrolidine | H | 2-Thiophene | 356 |
| 22 | 1-Pyrrolidine | H | 4-Tosyl | 396 |
| 23 | 1-Pyrrolidine | H | 3,5 difluoro Phenyl | 386 |
| 24 | 1-Pyrrolidine | H | 2,3 difluoro-Phenyl | 386 |
| 25 | 1-Pyrrolidine | H | 3-Nitro-Phenyl | 395 |
| 26 | 1-Pyrrolidine | H | 4-Propylphenyl | 392 |
| 27 | 1-Pyrrolidine | H | 2,4,6 Trimethylphenyl | 392 |
| 28 | 1-Pyrrolidine | H | Methylenethiophenyl | 396 |
| 29 | 1-Pyrrolidine | H | 2,3,6 Trifluorophenyl | 404 |
| 30 | 1-Pyrrolidine | H | 3-Fluorophenyl | 368 |
| 31 | 1-Pyrrolidine | H | 2,3 Dichlorophenyl | 419 |
| 32 | 1-Pyrrolidine | H | 2,5 Difluorophenyl | 386 |
| 33 | 1-Pyrrolidine | H | 2,3,4 Trifluorophenyl | 404 |
| 34 | 1-Pyrrolidine | H | 3-Methoxy-Phenyl | 380 |
| 35 | 1-Pyrrolidine | H | 2-Trifluoromethyl Phenyl | 418 |
| 36 | 1-Pyrrolidine | H | 3,5 Dimethoxy-Phenyl | 410 |
| 37 | 1-Pyrrolidine | H | 3-Tolyl | 364 |
| 38 | 1-Pyrrolidine | H | 3-Cyano-Phenyl | 375 |
| 39 | 1-Pyrrolidine | H | 3,4,5 Trifluoro-Phenyl | 404 |
| 40 | 1-Pyrrolidine | H | 2,3,4,5 Tetrafluoro-Phenyl | 422 |
| 41 | 1-Pyrrolidine | H | Cyclobutyl | 328 |
| 42 | 1-Pyrrolidine | H | 2-Methoxy-Phenyl | 380 |
| 43 | 1-Pyrrolidine | H | 2-Tolyl | 364 |
| 44 | 1-Pyrrolidine | H | 2-Chlorophenyl | 384 |
| 45 | 1-Pyrrolidine | H | 4-Butyl-Phenyl | 406 |
| 46 | 1-Pyrrolidine | H | 2,6 Dichlorophenyl | 419 |

-continued

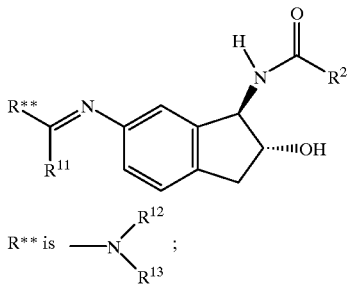

wherein R$^2$, R$^{11}$, R$^{12}$, and R$^{13}$ are defined as described supra.

| Comp. # | R** | R$^{11}$ | R$^2$ | Electrospray Ionization M. S. (M + 1) |
|---|---|---|---|---|
| 47 | 1-Pyrrolidine | H | 2,4,6 Trichloro-Phenyl | 453 |
| 48 | 1-Pyrrolidine | H | 2-Quinoxyl | 402 |
| 49 | 1-Pyrrolidine | H | 2,4,5 Trifluoro-Phenyl | 404 |
| 50 | 1-Pyrrolidine | H | 2,6 Difluoro-Phenyl | 386 |
| 51 | 1-Pyrrolidine | H | 2-Iodophenyl | 476 |
| 52 | 1-Pyrrolidine | H | 2,4 Difluorophenyl | 386 |
| 53 | 1-Pyrrolidine | H | Undecanyl | 414 |
| 54 | 1-Pyrrolidine | H | 4-Ethoxy-Phenyl | 394 |
| 55 | 1-Pyrrolidine | H | 4-Trifluormethyl-5-Fluoro-Phenyl | 436 |
| 56 | 1-Pyrrolidine | H | 2-Trifluoromethyl-6-Fluoro-Phenyl | 436 |
| 57 | Dimethyl-amine | H | Phenyl | 324 |
| 58 | Dimethyl-amine | H | 3,5 Dichlorophenyl | 393 |
| 59 | Dimethyl-amine | H | 4-Butoxy-Phenyl | 396 |
| 60 | Dimethyl-amine | H | 3,5 di-(trifluoromethyl)-Phenyl | 460 |
| 61 | Dimethyl-amine | H | 3-Cyano-Phenyl | 349 |
| 62 | Dimethyl-amine | H | Cyclopentyl | 316 |
| 63 | Dimethyl-amine | H | 2-Napthyl | 374 |
| 64 | Dimethyl-amine | H | 3-Trifluoromethyl-5-Fluoro-Phenyl | 410 |
| 65 | Dimethyl-amine | H | 3,4,5 Trifluoro-Phenyl | 378 |
| 66 | Dimethyl-amine | H | Trifluoromethyl | 316 |
| 67 | Dimethyl-amine | H | 4-Ethyl-Phenyl | 352 |
| 68 | Dimethyl-amine | H | 3-Chloro-2-Thiophene | 364 |
| 69 | Dimethyl-amine | H | 2-Benzothiophene | 380 |
| 70 | Dimethyl-amine | H | 4-Butyl-Phenyl | 380 |
| 71 | Dimethyl-amine | H | 1-Napthyl | 374 |
| 72 | Dimethyl-amine | H | 3,4 Dichloro-Benzenesulfonyl | 429 |
| 73 | Dimethyl-amine | H | 2-Chloro-3-Pyridinyl | 359 |
| 74 | Dimethyl-amine | H | 6-Chloro-3-Pyridinyl | 359 |
| 75 | Dimethyl-amine | H | 4-Trifluoromethyl-Phenyl | 392 |
| 76 | Dimethyl-amine | CH$_3$ | 3,4 Dichlorophenyl | 407 |
| 77 | 1-Piperidine | H | 3,4 Dichlorophenyl | 433 |
| 78 | 1-Piperidine | H | 3-Trifluoromethoxy-Phenyl | 448 |
| 79 | 1-Piperidine | H | 3-Fluorophenyl | 382 |
| 80 | 1-Piperidine | H | 3-Chlorophenyl | 398 |

-continued

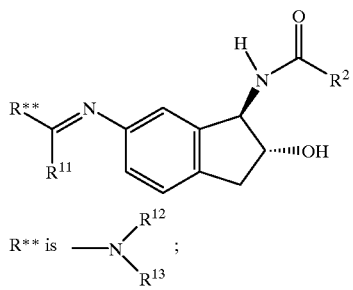

R** is wherein $R^2$, $R^{11}$, $R^{12}$, and $R^{13}$ are defined as described supra.

| Comp. # | R** | $R^{11}$ | $R^2$ | Electrospray Ionization M. S. (M + 1) |
|---|---|---|---|---|
| 81 | 1-Piperidine | H | 3-Methoxy-Phenyl | 394 |
| 82 | 1-Piperidine | H | 3-Trifluoromethyl-Phenyl | 432 |
| 83 | 1-Piperidine | H | 2-Tolyl | 378 |
| 84 | 1-Piperidine | H | 2,4 Dichlorophenyl | 433 |
| 85 | 1-Piperidine | H | 2-Chloro-4-Nitro-Phenyl | 444 |
| 86 | 1-Piperidine | H | 4-Propyl-Phenyl | 406 |
| 87 | 1-Piperidine | H | 4-Methoxyphenyl | 394 |
| 88 | 1-Piperidine | H | 2,3 Dichlorophenyl | 433 |
| 89 | 1-Piperidine | H | 3,4,5 Trifluorophenyl | 418 |
| 90 | 1-Piperidine | H | 3,5 Dimethoxy-Phenyl | 424 |
| 91 | 1-Piperidine | H | 3-Nitrophenyl | 409 |
| 92 | 1-Piperidine | H | 3,4 Difluorophenyl | 400 |

-continued

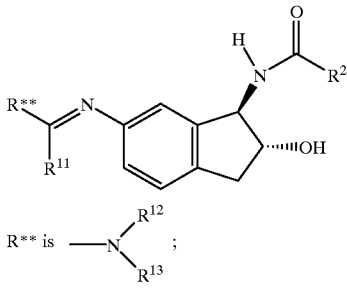

R** is wherein $R^2$, $R^{11}$, $R^{12}$, and $R^{13}$ are defined as described supra.

| Comp. # | R** | $R^{11}$ | $R^2$ | Electrospray Ionization M. S. (M + 1) |
|---|---|---|---|---|
| 93 | 1-Piperidine | H | 3,5 di(trifluoromethyl)-Phenyl | 500 |
| 94 | 1-Piperidine | H | 3,4 Dimethoxyphenyl | 424 |
| 95 | 1-Piperidine | H | 4-Cyano-Phenyl | 389 |
| 96 | 1-Piperidine | H | 4-Ethylphenyl | 392 |
| 97 | 1-Piperidine | H | 3,5 Dichlorophenyl | 433 |
| 98 | 1-Piperidine | H | 3,5 Difluorophenyl | 400 |
| 99 | 1-Piperidine | H | 3-Bromophenyl | 443 |
| 100 | 1-Piperidine | H | 4-Butylphenyl | 420 |
| 101 | 1-Piperidine | H | 3-Cyanophenyl | 389 |
| 102 | 1-Piperidine | H | 2-Iodophenyl | 490 |
| 103 | 1-Piperidine | H | Phenyl | 364 |
| 104 | 1-Piperidine | H | 4-Nitrophenyl | 409 |
| 105 | 1-Piperidine | H | Trifluomethyl | 356 |

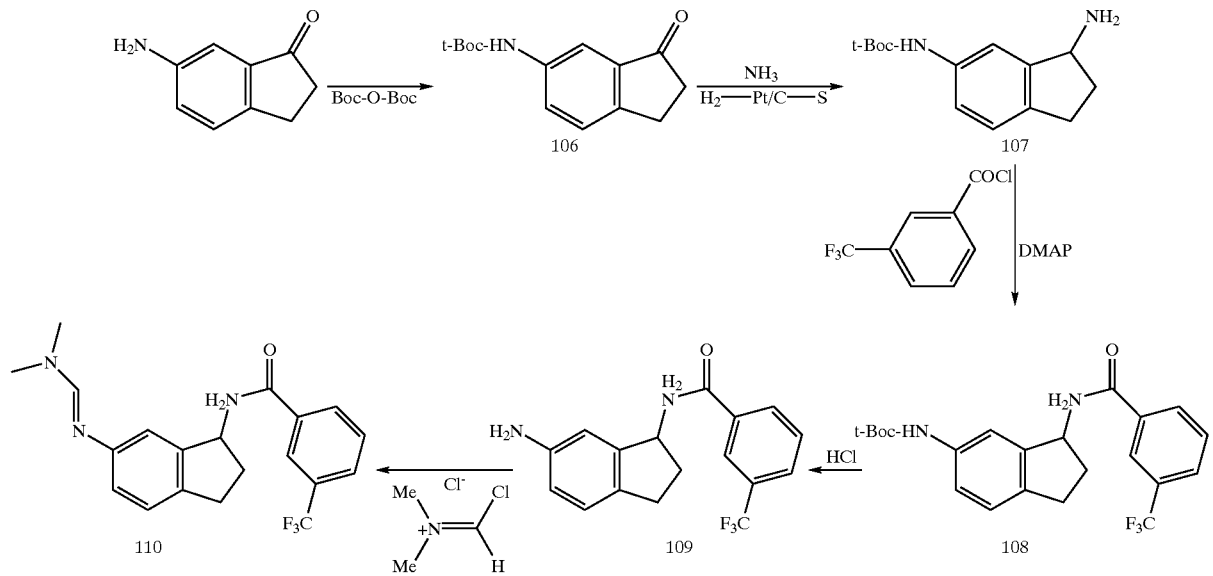

EXAMPLE 106

6-Amino-1-indanone t-butylcarbamate, 106

A mixture of 6-amino-1-indanone (4.41 g) and EtOAc (250 mL) was treated with di-t-butyl-di-carbonate (7.2 g) and the reaction stirred two days. After addition of $K_2CO_3$ (4 g), the reaction was heated to 70 C over night. The mixture was cooled and treated with cold $H_2O$ and extracted with EtOAc. The organics were washed with saturated aqueous citric acid and brine then the solvent was dried and evaporated to give a dark viscous oil that solidified. The material was further purified by hplc eluting with 20% EtOAc-hexane to give a floculant tan solid (5.1 g).

EXAMPLE 107

2-Amino-6-t-butylcarbamido-indane, 107

A mixture of 106 (2.5 g), THF (75 mL), ammonia (25 mL), and Pt/C-S (0.9 g) was treated with $H_2$ at 1000 psi for 8 h at 140 C. The catalyst was removed by filtration and the solvent evaporated to give a foam that was purified by radial chromatography eluting with 20% EtOH-2%-$NH_4OH$—$CHCl_3$ to give a white solid (0.9 g).

EXAMPLE 108

2-m-Trifluoromethylbenzamido-6-t-butylcarbamido-indane, 108

A solution of 107 (0.9 g) and a catalytic amount of 4-dimethylaminopyridine in pyridine (10 mL) was cooled in ice-water as m-trifluoromethylbenzoyl chloride (0.9 g) was added dropwise. The cooling was removed and the reaction was stirred over night. The solvent was evaporated, the residue treated with cold $H_2O$, and the mixture extracted with EtOAc. The extracts were washed with $H_2O$, 0.2 N HCl, $H_2O$, aqueous $NaHCO_3$, the solvent dried and then evaporated to give a white solid (1.42 g).

EXAMPLE 109

6-Amino-2-m-trifluromethylbenzamido-indane, 109

A solution of 108 (1.4 g) in EtOAc was cooled in ice-water and treated with a stream of dry HCl for 2 min. After another 10 min, the solvent was evaporated, the residue suspended in cold water, and the mixture made basic. The mixture was extracted with ether, the ether washed with brine, the solvent then dried and evaporated to give a white solid (1 g).

EXAMPLE 110

6-Dimethylformamidino-2-m-trifluoromethylbenamido-indane, 110

A mixture of chloromethylene-dimethylammonium chloride (0.1 g) and $CH_2Cl_2$ (5 mL) was treated with 109 (0.16 g). The reaction was then treated with triethylamine (0.3 mL) and after 5 min, the solvent was evaporated. The residue was treated with ice-water, the mixture was acidified, and the mixture extracted with ether. The aqueous phase was made basic, the mixture was extracted with ether, and the extracts washed with water and brine. The solvent was evaporated and the residue purified by radial chromatography eluting with 10% EtOH-$CHCl_3$. The HCl salt crystallized from EtOAc-acetone as a white solid (70 mg), m.p. 239 C, dec.

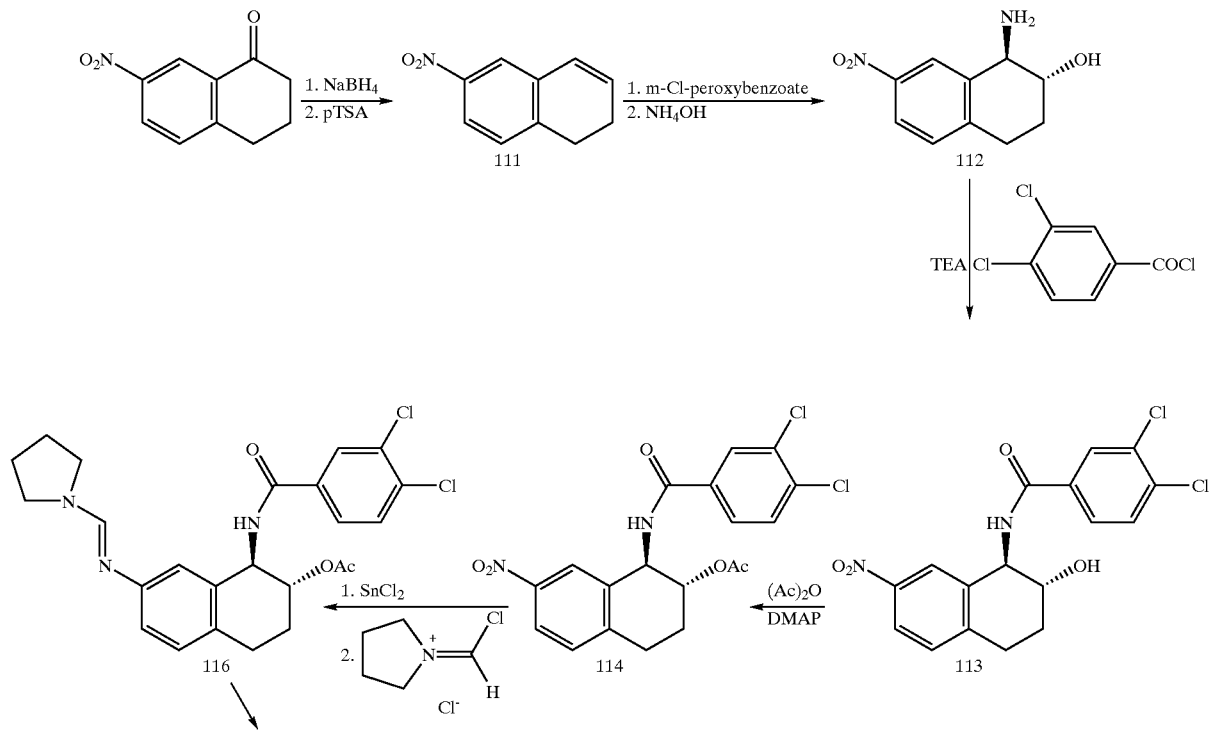

-continued

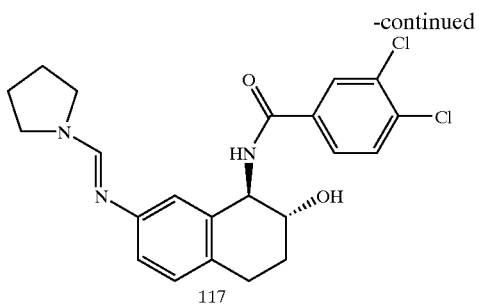

117

EXAMPLE 111

6-Nitro-1,2-dihydronapthalene, 111

A suspension of 7-nitrotetralone (20 g, 0.105 mol) in MeOH (300 mL) was treated with NaBH$_4$ (4.1 g) with intermitent cooling. After the addition, cooling was removed and the reaction stirred over night. The reaction was cooled in ice-water and quenched with a solution of MeOH (200 mL) and concentrated HCl (35 mL). The solvent was evaporated, the residue was suspended in H$_2$O, and the mixture was extracted with CHCl$_3$. The extracts were dried and the solvent evaporated to give a tan solid. A mixture of the solid, p-toluenesulfonic acid (0.4 g), and toluene (300 mL) was heated to reflux for over night with water being collected in a Dean-Stark trap. The reaction was cooled, washed with H$_2$O, aqueous NaHCO$_3$, and brine, then the solvent was dried and evaporated to give a dark liquid (15.6 g) that had an nmr consistent with the desired material.

EXAMPLE 112

(±)-Trans-1-amino-2-hydroxy-7-nitrotetraline, 112

A solution of 111 (15.6 g) in CH$_2$Cl$_2$ (400 mL) was cooled in ice-water and m-chloro-peroxybenzoic acid (42 g of 50–55% pure material) was added in portions over 1 h. Excess oxidant was then destroyed with aqueous sodium thiosulfate. The reaction was filtered and the organics washed with aqueous NaHCO$_3$ and brine, then the solvent was dried and evaporated to give a yellow solid (16.9 g). The solide was suspended in ammonium hydroxide (550 mL) and the mixture heated to 55° C. for 72 h. The solid was collected by filtration and recrystallized from MeOH to give a floculant white solid, m.p. 216–218° C. (12.3 g).

EXAMPLE 113

(±)-Trans-1-(3,4-dichlorobenzamido)-2-hydroxy-7-nitrotetraline, 113

A solution of 112 (2.1 g) in warm THF (300 mL) was treated with triethylamine (5 mL) and the solution allowed to come to room temperature. A solution of 3,4-dichlorobenzoyl chloride (2.3 g) in THF (50 mL) was added dropwise over 20 min. After stirring over night, the solvent was evaporated to give a solid (3.97 g) that had the appropriate nmr spectrum.

EXAMPLE 114

(±)-Trans-1-(3,4-dichlorobenzamido)-2-acetoxy-7-nitrotetraline, 114

A mixture of 113 (1.9 g, 0.005 mol) in THF (200 mL), triethylamine (1.3 mL), and a catalystic amount of 4-dimethylaminopyridine was treated with acetic anhydride (0.9 mL). After stirring over night, the solvent was evaporated and the residue treated with H$_2$O. After 2 h, the mixture was extracted with EtOAc. The extracts were washed with 1 N H$_2$SO$_4$, brine, aqueous NaHCO$_3$, and brine, then the solvent was dried and evaporated to give a floculant white solid (1.94 g) that had the appropriate nmr for the desired material.

EXAMPLE 115

(±)-Trans-1-(3,4-dichlorobenzamido)-2-acetoxy-7-aminotetraline, 115

A solution of 114 (1.9 g) in DMF (100 mL) was treated with SnCl$_2$–2H$_2$O (4 g). After 4 h, additional SnC$_2$–2H$_2$O (1 g) was added three times over three days. The solvent was then evaporated, the residue suspended in H$_2$O-EtOAc, the mixture neutralized with 5N NaOH, and the mixture filtered. The organics were separated, washed with brine, dried, and the solvent evaporated to give a brown foam (1.9 g).

EXAMPLE 116

(±)-Trans-1-(3,4-dichlorobenzamido)-2-acetoxy-7-(pyrrolidinoformamido)tetraline, 116

A solution of pyrrolidine carboxamide (1.5 mL) in CH$_2$Cl$_2$ (25 mL) was treated with POCl$_3$ (0.23 mL). After 1.5 h, the solution was treated with triethylamine (1 mL) and 115 (0.5 g). After stirring over night, the solvent was evaporated, the residue was treated with ice-water, the mixture neutralized, and the mixture extracted with EtOAc. The extracts were washed with brine and the solvent was dried and evaporated to give a dark oil. The oil was purified by radial chromatography eluting with 5% EtOH—CHCl$_3$ to give a tan solid that was recrystallized from EtOAc to give a white solid (0.18 g), m.p. 229° C., dec.

EXAMPLE 117

(±)-trans-1-(3,4-dichlorobenzamido)-2-hydroxy-7-(pyrrolidinoformamido)tetraline, 117

A solution of 116 (0.27 g) in MeOH (10 mL) was treated with 0.135 M sodium methoxide (4.9 mL) in MeOH. After 4 h, the solvent was evaporated, the residue was suspended in H$_2$O, and the solid was collected by filtration. The solid was crystallized from EtOAc-ether to give a tan powder, m.p. 206–208° C.

EXAMPLES 118–133

The structures of Examples 118–133 are presented as follows. The compound number corresponds to both the compound number and the Example number.

EXAMPLE 118
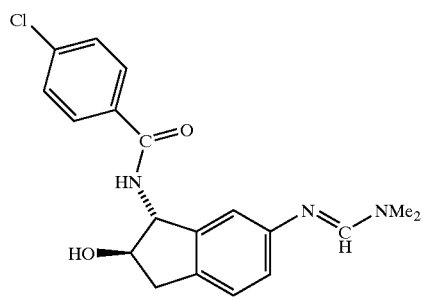
EXAMPLE 119
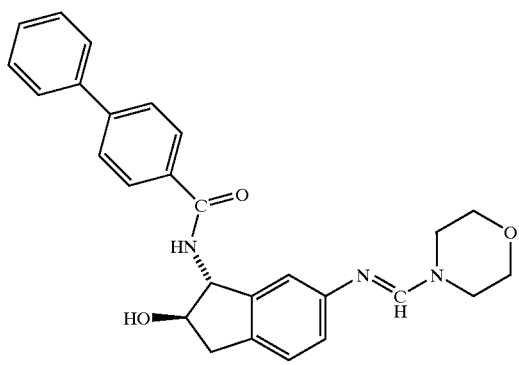
EXAMPLE 120
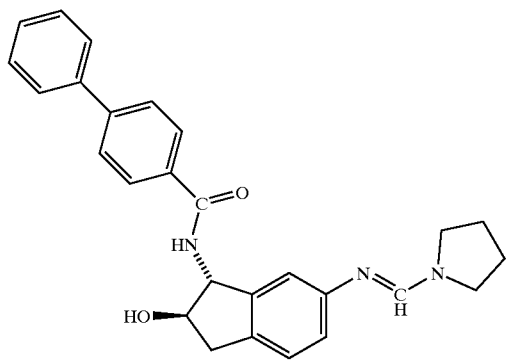
EXAMPLE 121
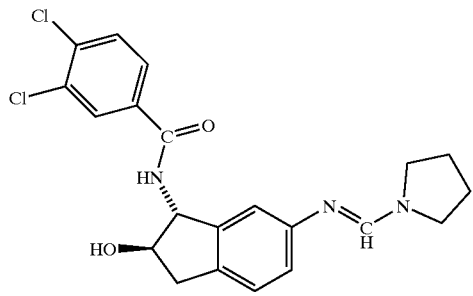
EXAMPLE 122
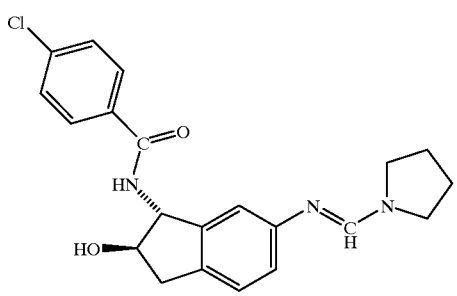
EXAMPLE 123
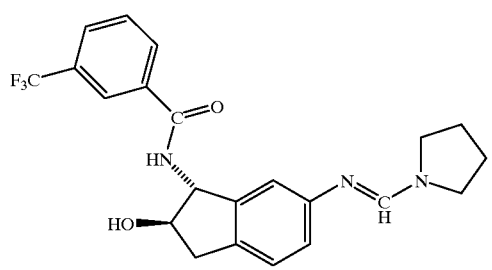
EXAMPLE 124
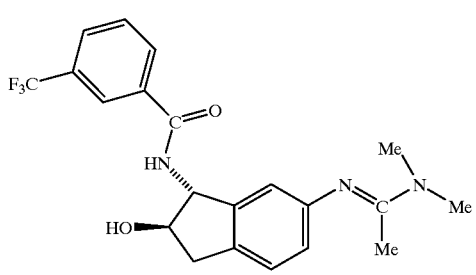
EXAMPLE 125
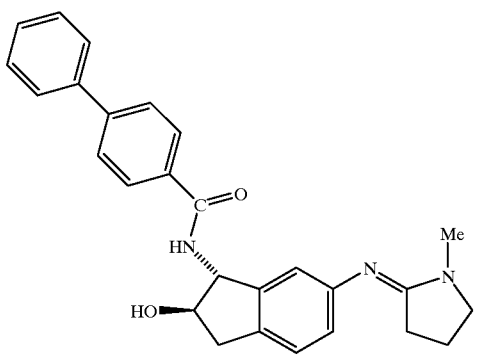

EXAMPLE 126
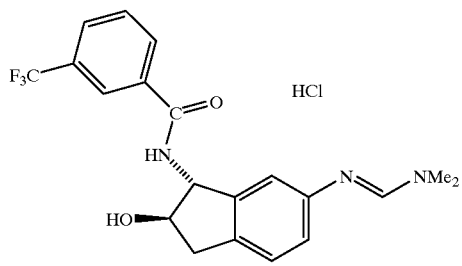
EXAMPLE 127
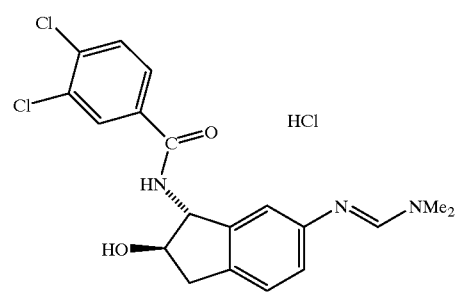
EXAMPLE 128
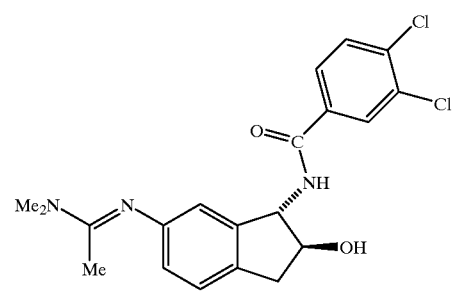
EXAMPLE 129
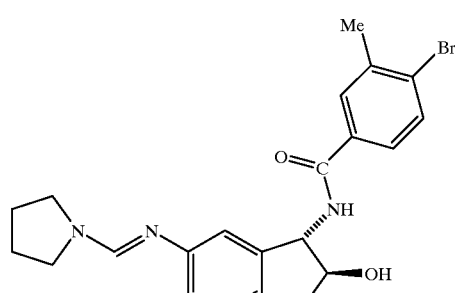
EXAMPLE 130
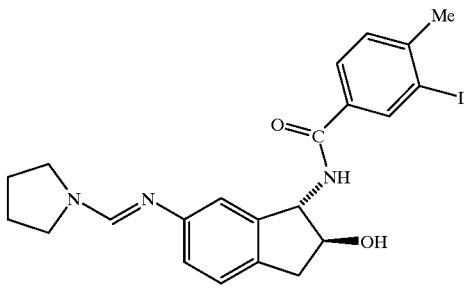
EXAMPLE 131
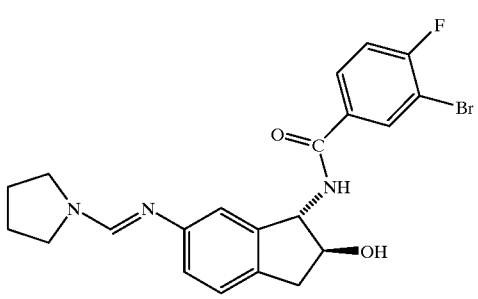
EXAMPLE 132
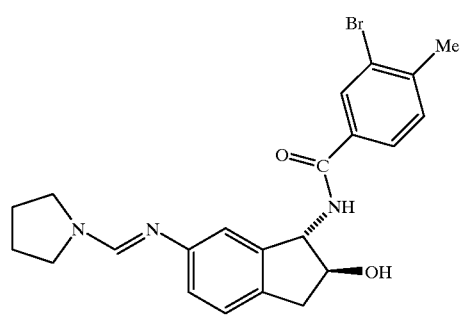
EXAMPLE 133
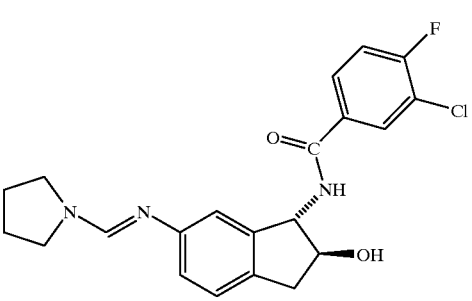

EXAMPLE 134

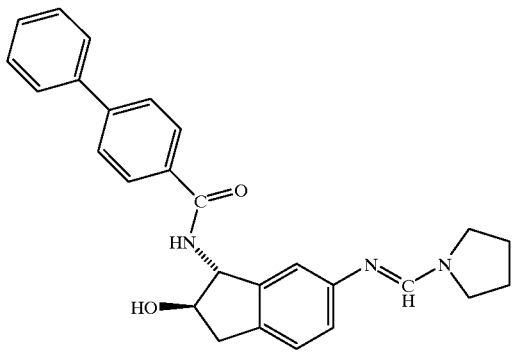

That which is claimed is:

1. A compound of the Formula V:

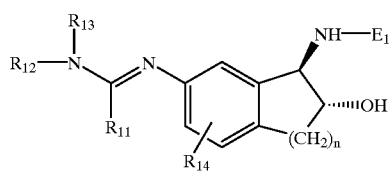

$E_1$ is selected from the group consisting of $C_1$–$C_{10}$ alkyl; substituted $C_1$–$C_{10}$ alkyl wherein the alkyl group is substituted with from one to five substituents selected from the group consisting of $C_2$–$C_6$ alkenyl, halo, —$CF_3$, —$OR^{4a}$, —$SR^{5a}$, —$CO2R^{6a}$, $C_3$–$C_8$ cycloalkyl, and —CN; wherein $R^{4a}$, $R^{5a}$, and $R^{6a}$ are each independently selected from the group consisting of hydrogen, $C_1$–$C_3$ alkyl, and phenyl; $C_2$–$C_{10}$ alkenyl; $C_3$–$C_8$ cycloalkyl; aryl selected from the group consisting of phenyl and naphthyl; substituted aryl wherein the aryl group is selected from the group consisting of phenyl and naphthyl and is substituted with from one to three substituents selected from the group consisting of halogen(s), —$CF_3$, $NO_2$, —CN, $C_{1-15}$-alkyl, $C_{2-5}$-alkenyl, $C_{2-5}$-alkynyl, —$COR^{6a'}$, —$OR^{4a'}$, —$SR^{5a'}$, $C_3$–$C_8$ cycloalkyl, $C_5$–$C_8$ cycloalkenyl, and phenyl, wherein $R^{4a'}$, $R^{5a'}$, and $R^{6a'}$ are each independently selected from hydrogen, —$CF_3$, $C_1$–$C_3$ alkyl, phenyl, and —$C_1$–$C_3$ alkylphenyl and provided that there is not more than one substituent selected from the group consisting of phenyl, $C_3$–$C_8$ cycloalkyl, and $C_5$–$C_8$ cycloalkenyl; heteroaryl wherein the heteroaryl is optionally fused with a phenyl group and is selected from the group consisting of thiophene, pyrrole, furan, oxazole, pyrazole, imidazole, thiazole, purine, triazoles, thiadiazoles, pyridine, quinoline, isoquinoline, phenanthrine, 5,6-cycloheptenopyridine, pyridazines, cinnolines, phthalazines, pyrazines, pyrimidines, quinazolines; substituted heteroaryl wherein the heteroaryl group is optionally be fused with a phenyl group and is selected from the group consisting of thiophene, pyrrole, furan, oxazole, pyrazole, imidazole, thiazole, purine, triazoles, thiadiazoles, pyridine, quinoline, isoquinoline, phenanthrine, 5,6-cycloheptenopyridine, pyridazines, cinnolines, phthalazines, pyrazines, pyrimidines, quinazolines and is substituted at a carbon atom with a substituent selected from the group consisting of $C_{1-6}$-alkyl, —$CF_3$, phenyl, benzyl, and thienyl;

$R^{11}$ is selected from the group consisting of hydrogen and $C_1$–$C_3$ alkyl;

$R^{12}$ is independently selected from the group consisting of hydrogen, $C_1$–$C_{10}$ alkyl, and phenyl;

$R^{13}$ is independently selected from the group consisting of hydrogen, $C_1$–$C_{10}$ alkyl, and phenyl; or $R^{12}$ and $R^{13}$ together with the nitrogen to which they are attached form a group of the formula II:

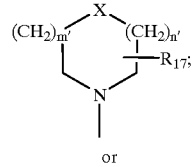

II' wherein the II' group is a group of Formula II which is unsaturated; or $R^{11}$ and $R^{12}$ together with the nitrogen and carbon to which they are bound can join to form a three to six membered ring;

$R^{14}$ is selected from the group consisting of H, halo, $C_1$–$C_3$ alkyl, and —$OR^{16}$;

$R^{16}$ is $C_1$–$C_3$ alkyl;

$R^{17}$ is independently selected from the group consisting of hydrogen, —$OR^{4'}$, —$SR^{5'}$, $C_1$–$C_3$ alkyl, $C_2$–$C_3$ alkenyl, halo, —CN, —$COR^{4b}$, and —OC(O)—$R^{15'}$;

$R^{4b}$ is selected from hydrogen and $C_1$–$C_3$ alkyl;

$R^{15'}$ is $C_1$–$C_3$ alkyl or phenyl;

$R^{4'}$ is hydrogen or $C_1$–$C_3$ alkyl;

$R^{5'}$ is hydrogen or $C_1$–$C_3$ alkyl;

X is selected from the group consisting of $CH_2$, O, S, NH, carbonyl, and a bond;

n' is 0 to 2;

m' is 0 to 2;

n is 0 to 3; or a pharmaceutically acceptable salt or solvate thereof.

2. A compound of claim 1 wherein n is 1.

3. A compound of claim 2 wherein the compound is trans.

4. A compound of claim 2 wherein $R^{12}$ and $R^{13}$ together with the nitrogen to which they are attached form a piperidine ring.

5. A compound of claim 2 wherein formula II is a pyrrolidine ring.

6. A compound of claim 2 wherein $R^{12}$ and $R^{13}$ are each independently selected from $C_1$–$C_3$ alkyl.

7. A compound of claim 1 wherein n is 2.

8. A pharmaceutical formulation comprising a compound of claim 1 and one or more pharmaceutically acceptable excipients therefor.

9. A method for treating a mammal suffering from or susceptible to a psychotic condition comprising administering to said mammal an effective amount of a compound of claim 1.

10. A method of treating a mammal suffering from or susceptible to a condition associated with the mediation of a muscarinic receptor, comprising, administering to said mammal an effective amount of a compound of claim 1.

11. A method for treating a mammal suffering from or susceptible to a condition which can be treated using a muscarinic receptor agonist, comprising administering to said mammal an effective amount of a compound of claim 1.

* * * * *